United States Patent
Ben Dror et al.

(10) Patent No.: US 8,052,992 B2
(45) Date of Patent: Nov. 8, 2011

(54) GLYCEROPHOSPHOLIPIDS CONTAINING OMEGA-3 AND OMEGA-6 FATTY ACIDS AND THEIR USE IN THE TREATMENT AND IMPROVEMENT OF COGNITIVE FUNCTIONS

(75) Inventors: Gai Ben Dror, Moshav Ofer (IL); Dorit Plat, Shimshit (IL); Orly Farkash, Shimshit (IL); Rassan Zuabi, Afula (IL); Zohar Bar-On, Ramat Zvi (IL); Avidor Shulman, Kiryat Tivon (IL); Dori Pelled, Hod Hasharon (IL)

(73) Assignee: Enzymotec Ltd., Migdal Haemeq (IL)

( * ) Notice: Subject to any disclaimer, the term of this patent is extended or adjusted under 35 U.S.C. 154(b) by 0 days.

(21) Appl. No.: 11/414,150

(22) Filed: Apr. 28, 2006

(65) Prior Publication Data

US 2006/0241080 A1 Oct. 26, 2006

Related U.S. Application Data

(63) Continuation-in-part of application No. 10/994,175, filed on Nov. 19, 2004, now abandoned, which is a continuation of application No. PCT/IL2004/000957, filed on Oct. 21, 2004.

(30) Foreign Application Priority Data

Oct. 22, 2003 (IL) .......................................... 158552

(51) Int. Cl.
| | |
|---|---|
| A61K 47/00 | (2006.01) |
| A61K 35/60 | (2006.01) |
| A61K 36/02 | (2006.01) |
| A01N 57/26 | (2006.01) |
| C12P 13/00 | (2006.01) |
| C07F 9/02 | (2006.01) |

(52) U.S. Cl. .................... 424/439; 424/523; 424/195.17; 514/78; 435/128; 554/78

(58) Field of Classification Search .................... 514/78; 435/128; 554/78; 424/439, 523, 195.17
See application file for complete search history.

(56) References Cited

U.S. PATENT DOCUMENTS
5,015,483 A 5/1991 Haynes et al.
(Continued)

FOREIGN PATENT DOCUMENTS
DE 2907778 8/1979
(Continued)

OTHER PUBLICATIONS

Kidd, Parris, M., Phosphatidylserine; Membrane Nutrient for Memory. A Clinical and Mechanistic Assessment, Alternative Medicine Review, vol. 1, No. 2, 1996, pp. 70-84.*

(Continued)

*Primary Examiner* — Robert A Wax
*Assistant Examiner* — Aradhana Sasan
(74) *Attorney, Agent, or Firm* — John P. White; Cooper & Dunham LLP

(57) ABSTRACT

Disclosed herein is a lipid preparation, said preparation comprising a phosphatidylserine moiety, and poly-unsaturated fatty acid (PUFA) acyl groups, particularly long-chain poly-unsaturated fatty acid (LC-PUFA) acyl groups such as omega-3 and/or omega-6 acyl groups, wherein said PUFA is covalently bound to said glycerophospholipid. Said lipid preparations are particularly useful in the treatment of mental and cognitive disorders, e.g. ADHD (attention deficit hyperactivity disorder) and Alzheimer's disease.

The disclosed preparations present improved bioactivity, and are useful in the treatment of various cognitive and mental conditions and disorders, as well as for maintenance of normal functions of brain-related systems and processes.

9 Claims, 7 Drawing Sheets

U.S. PATENT DOCUMENTS

| | | | |
|---|---|---|---|
| 5,502,077 A * | 3/1996 | Breivik et al. | 514/560 |
| 5,700,668 A | 12/1997 | De Ferra et al. | |
| 5,750,572 A | 5/1998 | Bruzzese | |
| 5,925,669 A | 7/1999 | Katz et al. | |
| 6,005,004 A | 12/1999 | Katz et al. | |
| 6,514,973 B1 | 2/2003 | Buchholz et al. | |
| 6,541,043 B2 * | 4/2003 | Lang | 424/725 |
| 6,645,742 B2 | 11/2003 | De Ferra et al. | |
| 2002/0091103 A1 | 7/2002 | Stoll et al. | |
| 2004/0120985 A1 | 6/2004 | Geiss | |
| 2004/0234587 A1 | 11/2004 | Sampalis | |
| 2005/0130937 A1 * | 6/2005 | Ben Dror et al. | 514/78 |
| 2006/0241080 A1 | 10/2006 | Dror et al. | |
| 2007/0160659 A1 | 7/2007 | Plat et al. | |
| 2008/0085319 A1 | 4/2008 | Dror et al. | |
| 2008/0085320 A1 | 4/2008 | Dror et al. | |
| 2009/0074857 A1 * | 3/2009 | Dror et al. | 424/456 |

FOREIGN PATENT DOCUMENTS

| | | |
|---|---|---|
| DE | 199 17 249 A1 | 7/2000 |
| DE | 199 43 198 A 1 | 4/2001 |
| EP | 0209037 A1 | 1/1987 |
| EP | 0275224 B1 | 7/1993 |
| EP | 0275005 BI | 8/1993 |
| EP | 0 609 078 A1 * | 1/1994 |
| EP | 0609078 | 1/1994 |
| EP | 0819760 A1 | 1/1998 |
| EP | 0922707 A1 | 6/1999 |
| EP | 1213294 A1 | 6/2002 |
| EP | 1417211 B1 | 5/2007 |
| ES | 2088750 | 8/1996 |
| JP | 02-49723 | 2/1990 |
| JP | 03188088 | 8/1991 |
| JP | 06256179 | 9/1994 |
| JP | 06279311 | 10/1994 |
| JP | 07-17855 | 1/1995 |
| JP | 2000-516261 | 12/2000 |
| JP | 2001-122884 | 5/2001 |
| JP | 2001-354680 | 12/2001 |
| JP | 2002-241385 | 8/2002 |
| WO | WO 92/21335 | 12/1992 |
| WO | WO 96/37200 | 11/1996 |
| WO | WO 97/39759 | 10/1997 |
| WO | WO 00/23546 | 4/2000 |
| WO | WO 00/56869 | 9/2000 |
| WO | WO 01/82902 A1 | 11/2001 |
| WO | WO 01/84961 A2 | 11/2001 |
| WO | WO 02/102394 A2 | 12/2002 |
| WO | WO 03/088949 A2 | 10/2003 |
| WO | WO 2004/049907 | 6/2004 |
| WO | WO 2005/038037 | 4/2005 |

OTHER PUBLICATIONS

Peter A. Ahmann MD, et. al., Placebo-Controlled Evaluation of Ritalin Side Effects, Pediatrics, Jun. 1993, pp. 1101-1106, vol. 91, No. 6.

Semyon I. Aleynik et al., Polyenylphosphatidylcholine Protects Against Alcohol but Not Iron-Induced Oxidative Stress in the Liver, Alcoholism: Clinical and Experimental Research, 2000, pp. 196-206, vol. 24, No. 2.

Marabella A. Alhambra MD, et. al., EEG Biofeedback: A New Treatment Option for ADD/ADHD, Journal of Neurotherapy, 1995, pp. 39-43, vol. 1, No. 2.

American Psychiatric Association, Diagnostic and Statistical Manual of Mental Disorders (DSM-IV-TR), 1994, 4th Edition, Washington, DC.

Gwendolyn Barcelo-Coblijn et al., Modification by docosahexaenoic acid of age-induced alterations in gene expression and molecular composition of rat brain phospholipids, PNAS, Sep. 30, 2003, pp. 11321-11326, vol. 100, No. 20, The National Academy of Science of the USA.

Barkley, RA., Attention-Deficit Hyperactivity Disorder. A Handbook for Diagnosis and Treatment, 1990, Guilford Press, New York.

D. Benton et. al., The Influence of Phosphatidylserine Supplementation on Mood and Heart Rate when Faced with an Acute Stressor, Nutritional Neuroscience, 2001, pp. 169-178, vol. 4.

Arjan Blokland, PHD. et. al., Cognition-Enhancing Properties of Subchronic Phosphatidylserine (PS) Treatment in Middle-Aged Rats: Comparison of Bovine Cortex PS With Egg PS and Soybean PS Nutrition, 1999. pp. 778-783, vol. 15. Elservier Science.

Nicole Brossard et. al., Human plasma albumin transports [13C]docosahexaenoic acid in two lipid forms to blood cells, Journal of Lipid Research, 1997, pp. 1571-1582, vol. 38.

John R. Burgess et. al., Long-chain polyunsaturated fatty acids in children with attention-deficit hyperactivity disorder, Am. J. Clin. Nutri., 2000, pp. 327S-330S, vol. 71.

Irene Colquhoun et. al., A lack of Essential Fatty Acids as a Possible Cause of Hyperactivity in Children, Medical Hypotheses, 1981, pp. 673-679, vol. 7.

Julie A. Conquer et. al., Fatty Acid Analysis of Blood Plasma of Patients with Alzheimer's Disease, Other Types of Dementia, and Cognitive Impairment, Lipids, 2000, pp. 1305-1312, vol. 35, No. 12.

Marc Enslen et. al., Effect of Low Intake of n-3 Fatty Acids During Development on Brain Phospholipid Fatty Acid Composition and Exploratory Behavior in Rats, Lipids, 1991, pp. 203-208, vol. 26, No. 3.

Gordon B. Forbes, Clinical Utility of the Test of Variables of Attention (TOVA) in the Diagnosis of Attention-Deficit/Hyperactivity Disorder, Journal of Clinical Psychology, 1998, pp. 461-476, vol. 54, No. 4, John Wiley & Sons, Inc.

Charles H. Goyette. et. al., Normative Data on Revised Conners Parent and Teacher Rating Scales, Journal of Abnormal Child Psychology, 1978, pp. 221-236, vol. 6, No. 2.

Pnina Green et. al., Modulation of Fetal Rat Brain and Liver Phospholipid Content by Intraamnlotic Ethyl Docosahexaenoate Administration, Journal of Neurochemistry, 1995, pp. 2555-2560, vol. 65, No. 6, Lippincott-Raven Publishers, Philadelphia.

Lawrence M. Greenberg et. al., Developmental Normative Data on the Test of Variables of Attention (T.O.V.A), J. Child Psychol. Psychiatry, 1993, pp. 1019-1030, vol. 34, No. 6.

Tomohito Hamazaki et. al., Administration of Docosahexaenoic Acid Influences Behavior and Plasma Catecholamine Levels at Times of Psychological Stress, Lipids, 1999, pp. S33-S37, vol. 34, Supplement.

Tony Hayek et. al., Increased Plasma and Lipoprotein Lipid Peroxidation in Apo E-Deficient Mice, Biochemical and Biophysical Research Communications, Jun. 30, 1994, pp. 1567-1574, vol. 201, No. 3, Academic Press, Inc.

S. Hirayama et. al., Effect of docosahexaenoic acid-containing food administration on symptoms of attention-deficit/hyperactivity disroder—a placebo-controlled double-blind study, European Journal of Clinical Nutrition, 2004, pp. 467-473, vol. 58, Nature Publishing Group.

Barbara V. Howards, PHD. et. al., Low-Fat Dietary Pattern and Risk of Cardiovascular Disease, JAMA, Feb. 8, 2006, pp. 655-666, vol. 295, No. 6, American Medical Association.

FDA/ Center for Food Safety & Applied Nutrition, Final Decision Letter written by Christine L. Taylor, PHD., Phoshalidylserine and Cognitive Dysfunction and Dementia (Qualified Health Claim: Final Decision Letter), Office of Nutrition Products, Labeling and Dietary Supplements, U.S. Food & Drug Administration, May 13, 2003.

Yoko Irukayama Tomobe et. al., The Activity of Docosahexaenoic Acid (DHA)-rich Phospholipid was different from that of DHA-rich Triacylglycerol in Spontaneously Hypertensive Rats, J. Oleo Sci., 2001, pp. 945-950 (also numbered pp. 25-30), vol. 50, No. 12.

Miho Itomura et. al., The effect of fish oil on physical aggression in schoolchildren—a randomized, double-blind, placebo-controlled trial, Journal of Nutritional Biochemistry, 2005, pp. 163-171, vol. 16, Elsevier Inc.

B. L. Jorissen et. al., The Influence of Soy-derived Phosphatidylserine on Cognition in Age-Associated Memory Impairment, Nutritional Neuroscience, 2001, pp. 121-134, vol. 4.

Katbi J. Kemper, MD, MPH, Editorials, Dietary supplements for attention-deficit/hyperactivity disorder—a fishy business?, The Journal of Pediatrics, Aug. 2001, pp. 173-174, vol. 139, No. 2.

Shlomo Keidar, Anglotensin, LDL Peroxidation and Atherosclerosis, Life Sciences, 1998, pp. 1-11, vol. 63, No. 1, Elsevier Science, Inc.

Parris M. Kidd, PHD., Attention Deficit/Hyperactivity Disorder (ADHD) in Children: Rationale for Its Integrative Management, Alternative Medicine Review, 2000, pp. 402-428, vol. 5, No. 5, Thome Research, Inc.

Dominique Lemaitre-Delaunay, et. al., Blood compartmental metabolism of docosahexaenoic acid (DHA) in humans after ingestion of a single dose of (13C)DHA in phosphatidylcholine, Journal of Lipid Research, 1999, pp. 1867-1874, vol. 40.

Ann-Marie Lyberg, et. al., Monitoring the Oxidation of Docosahexaenoic Acid in Lipis, Lipids, 2005, pp. 969-979, vol. 40, No. 9.

Mark A. McDaniel, et. al., "Brain-Specific" Nutrients: A Memory Cure?, Psychological Science in the Public Interest, May 2002, pp. 12-38, vol. 3, No. 1, American Psychological Society.

E. A. Mitchell, et. al., Clinical Characteristics and Serum Essential Fatty Acid Levels in Hyperactive Children, Clinical Pediatrics, Aug. 1987, pp. 406-411, vol. 26, No. 8.

Frits A. J. Muskiet, et. al., Is Docosahexaenolc Acid (DHA) Essential? Lessons from DHA Status Regulations, Our Ancient Diet, Epidemiology and Randomized Controlled Trials, American Society for Nutritional Sciences, J. Nutr., 2004, pp. 183-186, vol. 134.

Ryuichi Nakashima, et. al., Synthesis of Didocosahexaenoylphosphatidylserine, Biosc. Biotech. Biochem., 1997, pp. 1991-1994, vol. 61, No. 12.

S. Reisbick, et. al., Home Cage Behavior of Rhesus Monkeys With Long-Term Deficiency of Omega-3 Fatty Acids, Physiology & Behavior, 1994, pp. 231-239, vol. 55, No. 2, Elsevier Science Ltd.

A. J. Richardson, et. al., The potential role of fatty acids in attention-deficit/hyperactivity disorder, Prostaglandins, Leukotrienes and Essential Fatty Acids, 2000, pp. 79-87, vol. 63 (1/2); Hardcourt Publishers Ltd.

Thomas A. Rugino, MD, et. al., Effects of Modafinil in Children With Attention-Deficit/Hyperactivity Disorder: An Open-Label Study, J. Am. Acad. Child Adolesc. Psychiatry, Feb. 2001, pp. 230-235, vol. 40, No. 2.

Jin-Hyans Song et. al., Oxidative Stability of Docosahexaenoic Acid-containing Oils in the Form of Phospholipids, Triacylglycerols, and Ethyl Esters, Biosc. Biotech. Biochem., 1997, pp. 2085-2088, vol. 61, No. 12.

Laura J. Stevens, et. al., Essential fatty acid metabolism in boys with attention-deficit hyperactivity disorder, Am. J. Clin. Nutr., 1995, pp. 761-768, vol. 62, American Socierty for Clinical Nutrition.

Laura Stevens, et. al., EFA Supplementation in Children with Inattention, Hyperactivity, and Other Disruptive Behaviors, Lipids, 2003, pp. 1007-1021, vol. 38, No. 10.

C. A. Stewart, et. al., The Watermaze, Behavioural Neuroscience: A Practical Approach. 1993, Shagal A. ed., pp. 107-122, vol. 1, Oxford University Press, New York, NY.

James M. Swanson, et. al., Effect of Stimulant Medication on Children with Attention Deficit Disorder: A "Review of Reviews", Exceptional Children, Oct. 1993, pp. 154-162, vol. 60, No. 2.

Tomoyuki Tahara, et. al., Stimulation of interferon β Production of Cultured Cells by Phospholipids in Foodstuffs, Biosc. Biotech. Bioche., 1992, pp. 1465-1466, vol. 56, No. 9.

Kaoru Tochizawa, et. al., Effects of Phospholipids Containing Docosahexaenoic Acid on Differentiation and Growth of HL-60 Human Promyelocytic Leukimla Cells, J. Jpn. Oil Chem. Soc., 1997, pp. 383-390, vol. 46, No. 4.

G. Toffano, et. al., Pharmacological Properties of Phospholipid Liposomes, Pharmacological Research Communications, 1980, pp. 829-845, vol. 12, No. 9, Italian Pharmacological Society.

Robert G. Voigt MD, et. al., A randomized, double-blind, placebo-controlled trial of docosahexaenoic acid supplementation in children with attention-deficit/hyperactivity disorder, The Journal of Pediatrics, Aug. 2001, pp. 189-196, vol. 139, No. 2.

Nobuhiro Yamamoto, et. al., Effect of dietary alpha-lindenate/linoleate balance on brain lipid compositions and learning ability of rats, Journal of Lipid Research, 1987, pp. 144-151, vol. 28.

Shlomo Yehuda, et. al., Modulation of learning, pain thresholds, and thermoregulation in the rat by preparations of free purified alpha-linolenic and linoleic acids: Determination of the optimal omega3-to-omega6 ratio, Proc. Natl. Acad. Sci. USA, Nov. 1993. pp. 10345-10349, vol. 90.

Genevieve S. Young, et. al., Effect of randomized supplementation with high dose olive, flax or fish oil on serum phospholipid fatty acid levels in adults with attention deficit hyperactivity disorder, Reprod. Nutr. Dev., 2005, pp. 549-558, vol. 45.

Tsakiris, S. (1984) Z Naturforsch {Cl, 39 (11-12); 1196-8.

Kidd, Phosphatidylserine: Membrane Nutrient for Memory. A Clinical and Mechanistic Assessment, 1996, Alternative Medicine Review, vol. 1, No. 2, pp. 70-84.

Bligh and Dyer, (1959) Can. UJ. Biochem. Physiol. 37, 9,11-917.

Sakai M. (1996) Nutr Sci Vitaminol. (Tokyo) 42(2-1):47-54.

Carrie et al., (2000) J. Lipid Res. 41, 465-472.

Yabuuchi et al. (1968) J. Lipid Res. 9(1):65-7.

Wijendran et al (2002) Pediatr. Res. 51:265-272.

Lytle et al. (1992) Nutr Cancel.: 17(2):187-94.

Suzuki et al. (2000) Jpn. J. Pharrnacol. 84, 86-8.

Drago et al. (1981) Neurobiol Aging. 2(3):209-13.

Voigt et al. (2001) J. Pediatr.; 139(2):189-96.

Zanotti A. et al. (1986) Psychopharmacology (Berl). 90(2):274-5.

Pearce et al. (1998) Nature 396: 75-77.

Kolanowski et al. (2001) Int. J. Food Sci Nutr.: 52(6):469-76.

Stubberfield et al. (1999) J. Paediatr Child Health; 35:450-3.

Williams et al. (1980) J. Neurochem.; 35, 266-269.

Claro F. et al. (1999) Physiol Behan. 67(4):551-4.

Chalon, et al (1998) JNutr.; 128(12):2512-9.

Suzuki et al (2001) J. Nut. 131:2951-6.

Song et al., Enhanced level of n-3 fatty acid in membrane phospholipids induces lipid peroxidation in rats fed dietary docosahexaenoic acid oil, 2001, Atherosclerosis, 155, pp. 9-18.

O'Brien et al. (1964) J. Lipid Res. 5(3):329-38.

Furushiro M. et al. (1997) Jpn. J. Pharmacol. 75(4):447-50.

Patent Abstracts of Japan, vol. 018, No. 651 (C-1285), Dec. 9, 1994 & JP 06 256179 (Nipon Oil & Fats Co Ltd), Sep. 13, 1994.

Patent Abstract of Japan, vol. 1995 No. 01, Feb. 28, 1995 & JP 06 279311 (Sagami Chem Res Center; others:01) 4.

Database WPI, Sect. Ch, Week 199139 Derwent Pub Ltd, GB; XP002322994 & JP 03 188088 (Ajinomoto KK) Aug. 16, 1991.

Tochizawa, Kaoru et al: "Effects of phospholipids . . . cells", Nihon Yukagakkaishi, 46(4), 383-90, Coden: NIYUFC; ISSN: 1341-8327, 1997, XP008044295.

Nakashima R et al: "Synthesis of didocasahexaenoylphosphalidylserine", Bioscience Biotech. Biochem., Japan Soc. for Biosci., Biotech. and Agrochem. Tokyo JP, vol. 61, No. 12, 1997, pp. 1991-1994, XP 008044298.

Claims pending in Gai Ben Dror et al., U.S. Appl. No. 11/872,258, filed Oct. 15, 2007.

Claims pending in Gai Ben Dror et al., U.S. Appl. No. 11/872,440, filed Oct. 15, 2007.

Claims pending in Gai Ben Dror et al., U.S. Appl. No. 12/215,080, filed Jun. 24, 2008.

Claims pending in Gai Ben Dror et al., U.S. Appl. No. 11/872,440, filed Oct. 15, 2007.

Claims pending in Gai Ben Dror et al., U.S. Appl. No. 12/215,080, filed Jun. 24, 2008.

Office Action issued May 14, 2009 in connection with U.S. Appl. No. 11/872,440, filed Oct. 15, 2007.

Final Office Action issued Jan. 5, 2010 in connection with U.S. Appl. No. 11/872,440, filed Oct. 15, 2007.

Interview Summary issued May 12, 2010 in connection with U.S. Appl. No. 11/872,440, filed Oct. 15, 2007.

Notice of Allowance issued Jun. 3, 2010 in connection with U.S. Appl. No. 11/872,440, filed Oct. 15, 2007.

Office Action issued Mar. 16, 2010 in connection with U.S. Appl. No. 12/215,080, filed Jun. 24, 2006.

Jorissen et al. Safety of Soy-derived Phosphatidylserine in Elderly People, Nutritional Neurosciences, 2002 (5), pp. 337-343.

AMNI Phosphatidylserine Product Data, 1999.

International Search Report issued by the International Searching Authority on Mar. 25, 2010 in connection with International Application No. PCT/IL2009/000626.

Written Opinion of the International Searching Authority issued by the International Searching Authority (ISA/IL) in connection with International Application No. PCT/IL2009/000626.

Office Action issued Mar. 16, 2010 in connection with U.S. Appl. No. 10/572,782, filed Nov. 8, 2006.
Yamane. Enzyme Engineering for Lipids, Proc. Sat. Forum, Sustainable Agricultural System in Asia, Nagoya: Jun. (2002), pp. 61-68.
Office Action issued Mar. 30, 2009 in connection with U.S. Appl. No. 10/572,782, filed Nov. 8, 2006.
Lekh Raj Juneja et al. Conversion of phosphatidylcholine to phosphatidylserine by various phospholipases D in the presence of L- or D-serine, Biochimica et Biophysica Acta, 1003 (1987) 277-283, pp. 277-283.
Wu Wutong, Biochemistry 4$^{th}$ Edition, p. 149, and English translation 2000.
International Search Report issued by the International Searching Authority on Aug. 29, 2005 in connection with International Application No. PCT/IL2004/000895.
International Preliminary Report on Patentability issued by the International Searching Authority on Mar. 27, 2006 in connection with International Application No. PCT/IL2004/000895, Aug. 29, 2005.
Written Opinion of the International Searching Authority issued by the International Searching Authority (ISA/IL) in connection with International Application No. PCT/IL2004/000895 Aug. 29, 2005.
Sampalis et al. Evaluation of the Effects of Neptune Krill Oil on the Management of Premenstrual Syndrome and Dysmenorrhea, Alternative Medicine Review, 8:2 (2003) pp. 171-179.
Hanahan et al. Complex Lipids, Annual Rev. Biochem., 32:215 (1963).
Office Action issued Dec. 26, 2007 in connection with U.S. Appl. No. 10/485,094, filed Jul. 15, 2004.
Preliminary Amendment filed Jan. 26, 2004 in connection with U.S. Appl. No. 10/485,094, filed Jul. 15, 2004.
Youdim et al. Essential fatty acids and the brain: possible health implications, Int. J. Devl Neuroscience, 18:383 (2000).
Kalmijn et al. Dietary Fat Intake and the Risk of Incident Dementia in the Rotterdam Study, Annals of Neurology, 42:5 (1997) pp. 776-782.
Edwards et al. Omega-3 polyunsaturated fatty acid levels in the diet and in red blood cell membranes of depressed patients, Journal of Affective Disorders, 48:149-155 (1998).
Hosokawa et al. Conversion to Docosahexaenoic Acid-Containing Phosphatidylserine from Squid Skin Lecithin by Phospholipase D-Mediated Transphosphatidylation, J. Agric. Food Chem., 48:4550-4554 (2000).
Wiegand et al. Phospholipid Molecular Species of Frog Rod Outer Segment Membranes, Exp. Eye Res., 37:159-173 (1983).
Bell et al. Molecular Species Composition of the Major Diacyl Glycerophospholipids from Muscle, Liver, Retina and Brain of Cod (Gadus Morhua), Lipids, 26:8 (1991) pp. 565-573.
Henderson et al. Lipid Composition of the Pineal Organ from Rainbow Trout (*Oncorhynchus mykiss*), Lipids, 29:5 (1994) pp. 311-317.
U.S. Appl. No. 60/307,842, filed Jul. 27, 2001 (Sampalis).
Japanese Office Action issued Feb. 1, 2011 in connection with Japanese Patent Application No. 2006-536258.
Werkman et al., A Randomized Trial of Visual Attention of Preterm Infants Fed Docosahexaenoic Acid Until Nine Months. Lipids 1996; vol. 31(1): 91-97.
Korean Office Action issued May 27, 2011 in connection with Korean Patent Application No. 10-2006-7007683.
Peet et al., Two double-blind placebo-controlled pilot studies of eicosapentaenoic acid in the treatment of schizophrenia. Schizophrenia Research Apr. 2001; vol. 49(3): 243-251.
Chinese Decision on Rejection issued Jun. 1, 2011 in connection with Chinese Patent Application No. 200480038107.X.
Canadian Office Action issued Jul. 14, 2011 in connection with Canadian Patent Application No. 2,542,504.

* cited by examiner

GLYCEROPHOSPHOLIPIDS CONTAINING OMEGA-3 AND OMEGA-6 FATTY ACIDS AND THEIR USE IN THE TREATMENT AND IMPROVEMENT OF COGNITIVE FUNCTIONS

CROSS REFERENCE TO RELATED APPLICATIONS

This application is a Continuation in Part of U.S. patent application Ser. No. 10/994,175 filed Nov. 19, 2004, which is a Continuation of International Patent Application No. PCT/IL2004/000957 filed Oct. 21, 2004.

FIELD OF THE INVENTION

The present invention relates to phospholipids and polar lipids preparations which are enriched with omega-3 and/or omega-6 fatty acids covalently attached to the lipid backbone, and particularly to their role in the improvement of cognitive functions.

BACKGROUND OF THE INVENTION

All publications mentioned throughout this application are fully incorporated herein by reference, including all references cited therein.

Lipids, and especially polar lipids, nitrogen containing lipids, and carbohydrate containing lipids (phospholipids, sphingosines, glycolipids, ceramides, sphingomyelins) are the major building blocks of cell membranes, tissues, etc. Additionally they play important roles in signal transduction processes and in a variety of biochemical and biosynthetic pathways.

Glycerophospholipids, lipids based on a glycerol backbone and containing a phosphate head group, are the main building blocks of cell membranes. Since most, if not all, biochemical processes involve cell membranes, the structural and physical properties of membranes in different tissues is crucial to the normal and efficient functioning of membranes in all biochemical processes.

Other important constituents of biological membranes are cholesterol, glycolipids, and peripheral and integral proteins. The basic structure of biological membranes is thus a series of recurrent unities of lipid-protein complexes. The membrane is asymmetric. The function of the external (cellular) and internal (sub cellular) membrane systems depends on their composition and on the integrity of their phospholipid structure. In addition to their presence in cell membranes, phospholipids constitute structural and functional elements of the surface mono-layers of lipoproteins and of surfactants.

Of utmost importance for the function of biological membranes is their fluidity, which is decisively influenced by phospholipids. Besides the content in cholesterol and proteins and the nature and charge of the polar head groups of phospholipids in the system, membrane fluidity depends on the length of the chains of fatty acid residues in the phospholipid molecule, as well as on the number and type of pairing of their double bonds.

Many health benefits have been attributed to the consumption of certain fatty acids. For example, it has been reported in many research studies that polyunsaturated fatty acids (PUFA) of the type omega-3 and omega-6, have several health benefits on cardiovascular disease, immune disorders and inflammation, renal disorders, allergies, diabetes, and cancer. These types of fatty acids are naturally occurring mainly in fish and algae, where they are randomly distributed on the sn-1, sn-2, and sn-3 positions of the glycerol backbone of triglycerides.

Extensive clinical studies investigating the importance of Docosahexaenoic acid (DHA; 22:6n-3), one of the most important omega-3 fatty acids, in the brain, found that low levels of DHA are associated with depression, memory loss, dementia, and visual problems, while a dramatic improvement in the elderly brain function has been observed as blood levels of DHA increase.

Fatty acid differences, including DHA have been shown in the brain of Alzheimer's patients as compared with normal age-matched individuals. Furthermore, low serum DHA is a significant risk factor for the development of Alzheimer's patients. Recently, it was shown [Conquer et al. (2000) Lipids; 35(12):1305-1312] in addition to Alzheimer's patients that in other dementias and cognitively impaired but non-demented individuals, there are low levels of n-3 fatty acids in the plasma. Suggesting that the decreased level of plasma DHA was not limited to the Alzheimer's disease patients but appears to be common in cognitive impairment with aging, and therefore may be a risk factor for cognitive impairment and/or dementia Other known benefits of DHA include: lower risk of arrhythmias, reduction in the risk of sudden cardiac death, lower plasma triglyceride levels and reduced blood clotting tendency. Furthermore, DHA may have importance in the field of brain functioning enhancement, baby formula fortification, diabetics and cancer.

The human body does not adequately synthesize DHA. Therefore it is necessary to obtain it from the diet. Humans obtain DHA from their diets, initially through the placenta, then from breast milk (or baby formula), and later through dietary sources, such as fish, red meats, animal organ meats and eggs. Popular fish like tuna, salmon and sardines are rich sources. Until recently, the primary source of DHA dietary supplements has been fish oils. The ability of enzymes to produce the omega-6 and omega-3 family of products of linoleic and alpha-linolenic acid, declines with age. Thus, because DHA synthesis declines with age, as people get older their need to acquire DHA directly from diet or supplements increases. In fact, several recent publications suggested DHA to be considered as an essential fatty acid [e.g. Muskiet, F. et al. (2004) J Nutr. 134(1):183-6].

Because DHA is important for signal transmission in the brain, eye and nervous system, many consumers concerned with maintaining mental acuity are searching for a pure, safe way to supplement their DHA levels.

Polyunsaturated acids, in particular long chain, such as omega-3 and 6, have been shown to confer many valuable health benefits on the population. The global market for long-chain PUFAs, including the food segment, is rapidly growing.

The majority of efforts in the industry are however invested in the improvement of PUFA processing techniques and in the creation of higher concentrated grades of PUFA derivatives to accommodate dietary supplements and functional foods needs.

PUFA-Lipids
PS-PUFA

Phosphatidylserine (PS) is the major acidic phospholipid in the brain, being one of the most important building blocks of cerebral cell membranes. The level of PS in brain cell membranes ensures their fluidity and functional structure, while guaranteeing normal and efficient signal transduction processes, efficient glucose consumption, and other biological pathways that result in normal cognitive and mental functions.

PS is a natural phospholipid with bio-functionality that has made it one of the most promising dietary supplements in the field of brain nutrition, for its properties in a variety of cognitive and mental functions. PS has been shown to improve memory, fight dementia and early stages of Alzheimer's disease, reduce stress and tension, improve attention span, enhance mood and fight depression, to name but few.

Since PS is not abundant in human nutrition. Moreover, the biosynthetic pathways responsible for the production of PS are malfunctioning in many people, especially the elderly, resulting in low levels of PS in the body and brain, which results in a variety of cognitive and mental disorders, such as depression, memory loss, short attention span, learning difficulties, etc. The supplementation of PS in the diets of elderly people with such disorders has resulted in dramatic improvements of these disorders. Over the recent years, studies have shown that even younger people can benefit from dietary supplementation of PS. PS has been shown to improve the learning capabilities of students, improve memory and attention span, etc.

Interestingly, early attempts to elucidate the role of DHA in rat developing brain had demonstrated that intra-amniotic injection of DHA to E17 fetal rats resulted with redistribution of total brain PL, and specifically 56.4% increase in PS-DHA abundance [Green et al. (1995) *J Neurochem;* 65(6):2555-25560].

It is therefore an object of the present invention to provide special preparations of PS, for use mainly as nutraceuticals and as functional food additives.

Studies conducted with PUFA-containing phospholipids have shown the following:

1. They are high-energy, basic, structural, and functional elements of all biological membranes, such as cells, blood corpuscles, lipoproteins, and the surfactant.

2. They are indispensable for cellular differentiation, proliferation, and regeneration.

3. They maintain and promote the biological activity of many membrane-bound proteins and receptors.

4. They play a decisive role for the activity and activation of numerous membrane-located enzymes, such as sodium-potassium-ATPase, adenylyle cyclase and lipoprotein lipase.

5. They are important for the transport of molecules through membranes.

6. They control membrane-dependent metabolic processes between the intracellular and intercellular space.

7. The polyunsaturated fatty acids contained in them, such as linoleic and linolenic acid, are precursors of the cytoprotective prostaglandins and other eicosanoids.

8. As choline and fatty acid donors they have an influence in certain neurological processes.

9. They emulsify fat in the gastrointestinal tract.

10. They are important emulsifiers in the bile.

11. They codetermine erythrocyte and platelet aggregation.

12. They influence immunological reactions on the cellular level.

Phospholipids containing PUFA are theoretically of importance in all those diseases in which damaged membrane structures, reduced phospholipid levels, and/or decreased membrane fluidity are present. This hypothesis is supported by experimental and clinical investigations of various membrane-associated disorders and illnesses.

Studies on the active principle as well as pharmacological and clinical trials are available on a variety of conditions and diseases related to membrane damage. For example in various liver diseases, hepatocyte structures are damaged by, for example, viruses, organic solvents, alcohol, medicaments, drugs, or fatty food. In consequence, membrane fluidity and permeability may be disturbed, and membrane-dependent metabolic processes as well as membrane-associated enzyme activities may be impaired, considerably inhibits liver metabolism.

Other examples include hyperlipoproteinemia with or without atherosclerosis, hemorrheological disturbances with an elevated cholesterol/phospholipid ratio in the membranes of platelets and red blood cells, neurological diseases, gastrointestinal inflammations, kidney diseases, and in a variety of aging symptoms.

All these very different diseases have in common comparable membrane disorders. With polyunsaturated phosphatidylcholine molecules such disorders may be positively influenced, eliminated, or even improved beyond normal due to the high content in polyunsaturated fatty acids. Following are some examples of the mechanisms that mediate this phenomenon:

1. High-density lipoprotein (HDL) particles enriched with PUFA-containing-phosphatidylcholine are able to take up more cholesterol from low-density lipoprotein (LDL) and tissues. More cholesterol can be transported back to the liver. This action on the cholesterol reverse transport is unique. All other lipid-lowering agents reduce either the cholesterol absorption in the body or the cholesterol synthesis in the liver and its distribution to the periphery. These substances, however, do not physiologically mobilize the cholesterol already present in the periphery.

2. The cholesterol/phospholipid ratio in membranes, platelets, and red blood cells decreases and membrane function is improved up to normalization.

3. Peroxidative reactions are reduced, damaged hepatocyte membrane structures restored, membrane fluidity and function stabilized, immuno-modulation and cell protection improved, and membrane-associated liver functions enhanced.

4. With the normalization of the cholesterol/phospholipid ratio, the bile is also stabilized.

5. Due to its specific property as a surface-active emulsifier, PUFA-containing-phosphatidylcholine solubilize fat and is used in reducing the risk and treatment of fat embolism.

6. The substitution with poly-unsaturated-fatty-acids and choline may have a cytoprotective effect in the brain and activate neuronal processes.

7. Liposomes with polyunsaturated phosphatidylcholine molecules may act as drug carriers, such as of vitamin E.

Some publications have reported preparations of phospholipids and suggested their use in neurological or psychiatric conditions.

WO 97/39759 discloses preparations comprising dieicosa-penta-noylphosphatidylcholine, didocosahexaenoylphosphatidylcholine, 1-eicosapenta-enoyl, 2-docosa-hexaenoylphosphatidylcholine, and 1-docosahexaenoyl, 2-eicosa-pentaenoylphosphatidylcholine, which are useful for treating bipolar disorders.

JP 06256179 discloses preparations comprising 1,2-diacyl-sn-glycerol derivatives of formula $R_1$-0-$CH_2$—CH($OR_2$)—$CH_2$-0-$R_3$ (I) wherein $R_1={14-24}C$ saturated or monoene fatty acid residue; $R_2$=a residue of arachidonic acid, eicosapentaenoic acid (EPA) or DHA; $R_3$=H, phosphorylcholine, phosphoryl-ethanolamine, phosphorylserine or phosphorylinositol, 1-Oleoyl-2-docosahexaenoyl-sn-glycero-3-phosphorylcholine that are effective components for improving learning ability and for treating senile dementia. However, none of the preparations disclosed in JP 06256179 comprises DHA.

JP 0627911 discloses phosphatidylserine derivatives of formula (I) and their salts wherein $R_1$=acyl residue of myristic, palmitic or stearic acid; $R_2$=acyl residue of linoleic, linolenic, arachidonic or docosahexaenic acid, and their use in the treatment of senile dementia accompanied with central nervous lesions, especially Alzheimer's disease. However said compositions do not comprise EPA as a possible substituent on the glycerophospholipid backbone.

The utilization of phospholipids enriched with PUFA holds many potential advantages from a clinical point of view. The phospholipid may deliver the essential fatty acid to specific organs or body parts, such as the brain, and assist in the incorporation of these fatty acids in membranes. Other advantages may arise from the fact that phospholipids enriched with PUFA will not have odor problems such as found in the major current nutraceutical source, the fish oils. Furthermore, some preliminary clinical studies have shown that PUFA incorporated in phospholipids possess superior efficacy than PUFA carried by triglycerides. [Song et al. (2001)*Atherosclerosis,* 155, 9-18].

Further studies have shown that the activity of DHA-rich phospholipids was different from that of DHA-rich triacylglycerols in spontaneously hypertensive rats [Irukayama-Tomobe et al. (2001) *Journal of Oleo Science,* 50(12), 945-950]. Spontaneously hypersensitive rats (SHR) were fed test lipid diets for six weeks, which contained 30%-DHA phospholipid (DHA-PL) extracted from fish roe or 30%-DHA fish oil (DHA-TG). The control diet contained corn oil in the presence of test lipids. After feeding, blood pressure in the DHA-TG and DHA-PL diet groups was found significantly lower compared to the control. Serum fatty acid content of dihomolinoleic acid (DHLnA) and Arachidonic acid (ARA; 20:4n-6) of the DHA-PL diet group was significantly less than the control or DHA-TG diet group. Serum triacylglycerol, phospholipid and total cholesterol in the DHA-TG and DHA-PL diet groups were significantly less than in the control. Liver total cholesterol in DHA-PL was twice that in the DHA-TG diet group and control.

Many PUFA-containing agents suffer from stability and quality problems due to the high degree of oxidation of the polyunsaturated fatty acids. These problems require the incorporation of antioxidants as well as the utilization of special measures which attempts to reduce this oxidation. The utilization of phospholipids as carriers of PUFA may result in enhanced stability of such products due to the anti-oxidative properties of phospholipids.

It seems that one of the most effective transport mechanisms for such essential fatty acids is the attachment of these groups to phospholipid molecules. The phospholipids have been shown to pass through the blood-brain barrier and transport the DHA where it is needed.

Organoleptic Concerns

PUFAs are traditionally extracted from coldwater fish. Despite the healthy image, one of the problems of consumer acceptance has been the resulting strong, fishy taste. To address this, microencapsulated forms of omega-3 have been pioneered in the last 15 years. A further step was the development of egg-containing products such as DHA-enriched mayonnaise and pasta. DHA-enriched yogurts, baked goods and broilers were also envisaged.

There is no other nutritional product or preparation that is considered to be an agent of PUFA delivery. All current commercial products are based on the fatty acids themselves in an encapsulated form or on foods enriched with PUFA through special animal/crop feed.

ADHD

Attention-deficit/hyperactivity disorder (ADHD) encompasses a broad constellation of behavioural and learning problems and its definition and diagnosis remain controversial [Kamper (2001) *J. Pediatr.* 139:173-4; Richardson et al. (2000) *Prostaglandins Leukot. Essent. Fatty Acids,* 63(1-2): 79-87]. The etiology of ADHD is acknowledged to be both complex and multi-factorial. Traditionally, ADHD is the diagnosis used to describe children who are inattentive, impulsive, and/or hyperactive. A conservative estimate is that 3-5% of the school-age population has ADHD [American Psychiatric Association (1994) *Diagnostic and statistical manual of mental disorders.* 4th ed. (DSM-IV) Washington, D.C.]. Roughly 20-25% of children with ADHD show one or more specific learning disabilities in math, reading, or spelling [Barkley, R. A. (1990) *Attention-deficit hyperactivity disorder: a handbook for diagnosis and treatment.* New York: Guilford Press]. Children with ADHD often have trouble performing academically and paying attention, and may be disorganized, have poor self-discipline, and have low self-esteem. Treatments for ADHD include behavior therapy and medications, mainly methylphenidate (Ritalin™). Psychostimulant drugs and antidepressants are often used to calm children with ADHD, with an effectiveness rate of ~75% [Swanson et al. (1993) *Except Child* 60:154-61]. The advantages of using these medications include rapid response, ease of use, effectiveness, and relative safety. Disadvantages include possible side effects, including decreased appetite and growth, insomnia, increased irritability, and rebound hyperactivity when the drug wears off [Ahmann et al. (1993) *Pediatrics;* 91:1101-6]. Moreover, these medications do not address the underlying causes of ADHD. Thus, studies to elucidate the potential contributors to the behavior problems in ADHD may lead to more effective treatment strategies for some children.

Omega-3 fatty acids are specifically implicated in maintaining central nervous system function. Deficiency of n-3 fatty acids in rats and monkeys has been associated with behavioral, sensory, and neurological dysfunction [Yehuda et al. (1993) *Proc. Natl. Acad. Sci. USA;* 90:10345-9; Reisbick et al. (1994) *Physiol. Behav.* 55:231-9; Enslen et al. (1991) *Lipids;* 26:203-8]. Several studies have focused on essential fatty acid metabolism in children with ADHD [Colquhoun et al. (1981) *Med Hypotheses;* 7:673-679]. Children with hyperactivity have been reported to be thirstier than normal children and have symptoms of eczema, asthma, and other allergies [Mitchell et al. (1987) *Clin. Pediatr.;* 26:406-11]. For example, in a cross-sectional study in 6 to 12-year-old boys recruited from central Indiana, it was showed that 53 subjects with ADHD had significantly lower proportions of key fatty acids in the plasma polar lipids ARA, eicosapentaenoic acid (EPA; 20:5n-3), and DHA and in red blood cell total lipids (20:4n-6 and 22:4n-6) than did 43 control subjects [Stevens et al. (1995) *Am. J. Clin. Nutr.;* 62:761-8]. However, recent publications investigating whether DHA supplementation would result in amelioration of the symptoms in ADHD children, suggested that careful attention should be paid as to which fatty acid(s) is used [Hirayama et al. (2004) *Eur. J. Clin. Nutr.;* 58(3):467-73; Voigt et al. (2001) *J Pediatr.;* 139 (2):189-96]. In these studies DHA supplementation had demonstrated only marginal if any beneficial effects.

Recently, it has been suggested that one of the possible solutions to the nutrient deficiencies which are common in ADHD, could be PS supplementation [Kidd (2000) *Altern Med Rev.;* 5(5):402-28].

It is therefore an object of the present invention to provide lipid preparations enriched with omega-3 or omega-6 fatty acids, for use mainly as nutraceuticals and as functional food additives. The composition of said preparation is such that it provides the preparation with the property of enhancing the bioavailability of PUFAs. Thus upon its consumption, preferably in the form of nutraceuticals, food additives or pharmaceutical compositions, the organism may, in the most efficient way, enjoy the benefits provided by said preparation, as will be described in detail below.

This and other objects of the invention will become apparent as the description proceeds.

SUMMARY OF THE INVENTION

In a first aspect, the present invention provides a lipid preparation being a mixture of glycerophospholipids, comprising a glycerophospholipid of formula I:

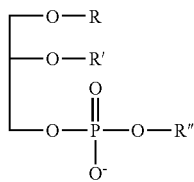

Formula I wherein R" represents a serine moiety, and R and R', which may be identical or different, independently represent hydrogen or an acyl group, wherein said acyl group is selected from saturated, mono-unsaturated or poly-unsaturated acyl groups (PUFA), particularly long-chain poly-unsaturated fatty acids (LC-PUFA), more preferably omega-3 and/or omega-6 acyl groups, and salts thereof, with the proviso that R and R' cannot simultaneously represent hydrogen, and wherein said LC-PUFA constitute at least 5% (w/w) of total fatty acids content of said preparation, preferably at least 8% (w/w), more preferably above 10% (w/w), and particularly 20-50% (w/w), said mixture optionally further comprising other glycerophospholipids, which are at least one of phosphatidylcholine, phosphatidylethalonamine, phosphatidylinositol, phosphatidylglycerol and phosphatidic acid, for use as an agent for the prevention, maintenance, improvement and/or treatment of a cognitive and/or mental condition in a subject in need, said condition being selected from the group consisting of Attention Deficit Disorder (ADD)/Attention Deficit Hyperactivity Disorder (ADHD), dyslexia, age-associated memory impairment and learning disorders, amnesia, mild cognitive impairment, cognitively impaired non-demented, pre-Alzheimer's disease, Alzheimer's disease, pre-dementia syndrome, dementia, age related cognitive decline, cognitive deterioration, moderate mental impairment, conditions that influence the intensity of brain waves and/or brain glucose utilization, stress, anxiety, concentration and attention impairment, mood deterioration, general cognitive and mental well being, neurodegenerative disorders and hormonal disorders.

In one embodiment, said lipid is one of a naturally occurring or a synthetic lipid.

In another embodiment, R represents hydrogen and R' represents an acyl group. Alternatively, R' represents hydrogen and R represents an acyl group.

In a further embodiment, said acyl group is at least one of an omega-3 acyl group, preferably selected from the group consisting of an eicosapentaenoyl (EPA), a docosahexaenoyl (DHA) group, and omega-3 alpha-linolenoyl group, and omega-6 acyl group, preferably selected from the group consisting of an arachidonoyl (ARA) group, an omega-6 linoleyl group, and an omega-6 gamma linoleyl group.

In one particular embodiment, said glycerophospholipid comprises both EPA and DHA, wherein the level of EPA is higher than the level of DHA. Alternatively, said glycerophospholipid comprises both EPA and DHA, and the ratio between EPA and DHA ranges from about 10:1 to 1:10, preferably from 5:1 to 1:5, more preferably from 3:1 to 1:3, most preferably between 1.5:1 to 1:1.5.

Most importantly, said glycerophospholipid substantially mimics the fatty acid composition and/or fatty acid profile of human brain phosphatidylserine (PS) and/or mammalian brain PS, and is derived from any one of marine, plant, animal or microorganism source. Alternatively, said glycerophospholipid is synthetic.

A synthetic glycerophospholipid may be prepared by enzymatic transphosphatidylation of a lipid source, said source selected from the group consisting of a marine, a plant, an animal and a microorganism source.

In an even further embodiment of the preparation of the invention, said glycerophospholipid is de-oiled.

Another essential feature of the lipid preparation of the invention is that said glycerophospholipid is effective at a lower dosage compared to soybean-PS, while having similar and/or improved bioactivity compared to soybean-PS.

In another aspect the present invention presents a lipid preparation being a mixture of glycerophospholipids, wherein said lipid has increased bioactivity compared to soybean-PS and/or LC-PUFA esterified to glyceride with or without glycerophospholipid, said mixture comprising a glycerophospholipid of formula I:

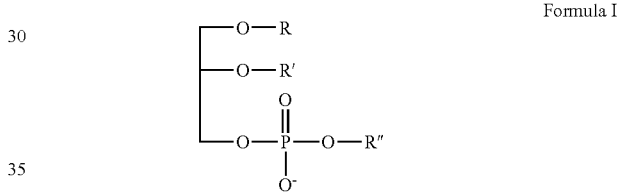

Formula I wherein R" represents a serine moiety, and R and R', which may be identical or different, independently represent hydrogen or an acyl group, wherein said acyl group is selected from poly-unsaturated acyl groups (PUFA), particularly long-chain poly-unsaturated fatty acids (LC-PUFA), more preferably omega-3 and/or omega-6 acyl groups, and salts thereof, with the proviso that R and R' cannot simultaneously represent hydrogen, and wherein said LC-PUFA constitute at least 5% (w/w) of total fatty acids content of said preparation, preferably at least 8% (w/w), more preferably above 10% (w/w), and particularly 20-50% (w/w), said mixture optionally further comprising other glycerophospholipids, for use in increasing the bioactivity of LC-PUFA and/or PS in mammalian tissues selected from the group consisting of brain, retina, liver, lung, plasma, and red blood cells, as compared with the bioavailability of LC-PUFA provided by a preparation containing LC-PUFA esterified to glycerides with or without glycerophospholipids.

Specifically, said lipid preparation is for use in the improvement or treatment of subjects suffering from Attention Deficit Disorder (ADD)/Attention Deficit Hyperactivity Disorder (ADHD), dyslexia, age-associated memory impairment and learning disorders, amnesia, mild cognitive impairment, cognitively impaired non-demented, pre-Alzheimer's disease, Alzheimer's disease, pre-dementia syndrome, dementia, age related cognitive decline, cognitive deterioration, moderate mental impairment, depression, Parkinson's disease, multiple sclerosis (MS), memory impairment and learning disorders, conditions that influence the intensity of brain waves and/or brain glucose utilization, aging, cognitive decline, stress, anxiety, child behavior disorders, concentration and attention disorders, mood deterioration, neurodegenerative disorders and hormonal disorders.

In a further aspect, the present invention provides a method of increasing the bioavailability of LC-PUFA in the mammalian tissue of a subject in need, said method comprising administering to said subject a therapeutically effective amount of the lipid preparation described herein, or a pharmaceutical composition comprising thereof, said lipid preparation being a mixture of glycerophospholipids, wherein said lipid has increased bioactivity compared to soybean-PS, said mixture comprising a glycerophospholipid of formula I as defined above, and wherein said LC-PUFA constitute at least 5% (w/w) of total fatty acids content of said preparation, preferably at least 8% (w/w), more preferably above 10% (w/w), and particularly 20-50% (w/w), said mixture optionally further comprising other glycerophospholipids.

In an even further aspect the present invention provides a method of treatment of a cognitive and/or mental condition selected from the group consisting of Attention Deficit Disorder (ADD)/Attention Deficit Hyperactivity Disorder (ADHD), dyslexia, age-associated memory impairment and learning disorders, amnesia, mild cognitive impairment, cognitively impaired non-demented, pre-Alzheimer's disease, Alzheimer's disease, pre-dementia syndrome, dementia, age related cognitive decline, cognitive deterioration, moderate mental impairment, depression, Parkinson's disease, multiple sclerosis (MS), memory impairment and learning disorders, conditions that influence the intensity of brain waves and/or brain glucose utilization, aging, cognitive decline, stress, anxiety, child behavior disorders, concentration and attention disorders, mood deterioration, neurodegenerative disorders and hormonal disorders, said method comprising administering to a subject in need a therapeutically effective amount of the lipid preparation defined in the invention or a pharmaceutical composition comprising thereof.

Said therapeutically effective amount may also be delivered in the form of a nutraceutical composition or a food article comprising said lipid preparation described in the invention.

Figure 1:
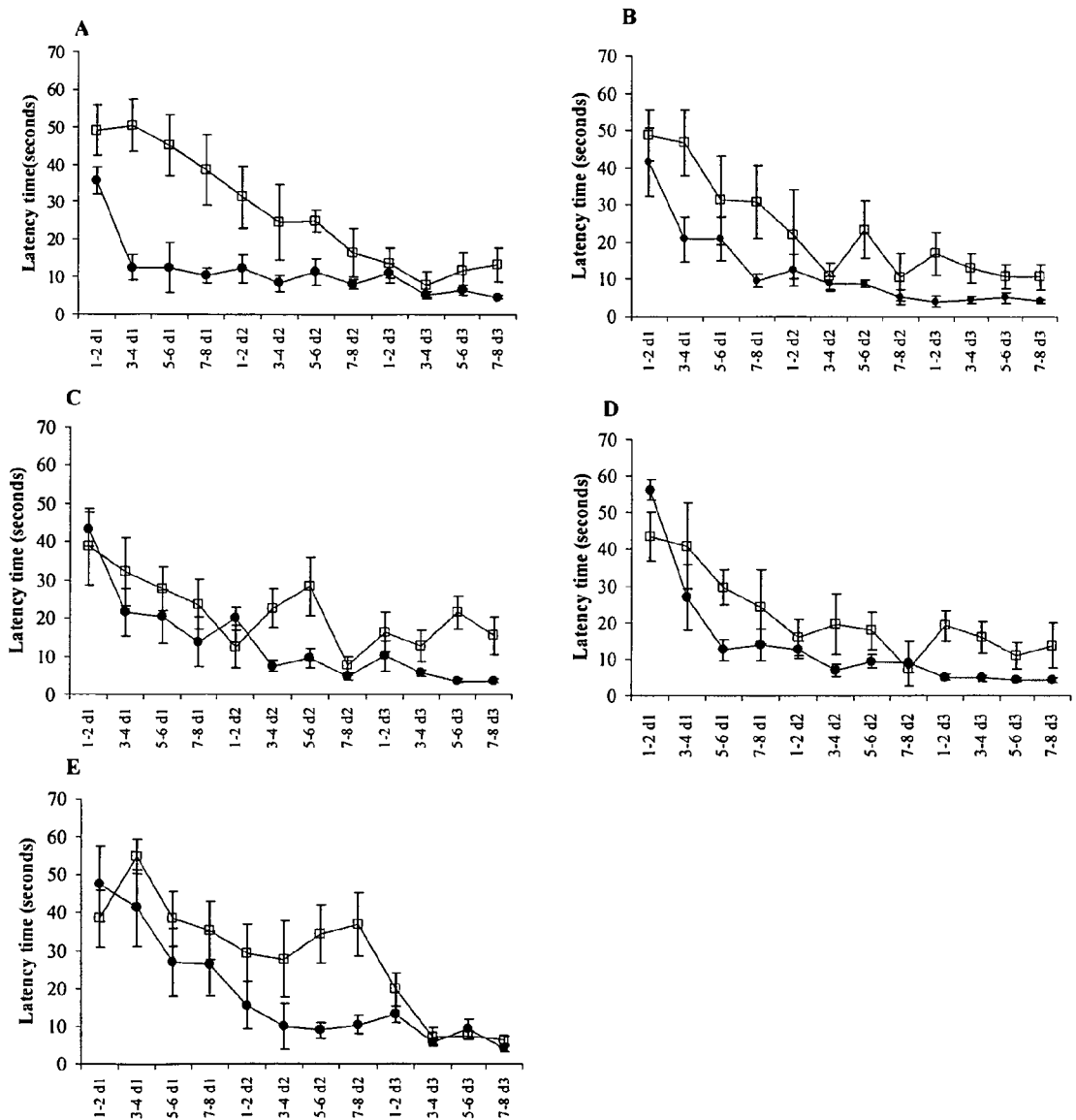
FIG. 1A-1E: Performance of rats in acquisition of the spatial Morris maze task.

Latency time to platform in the three days of acquisition (2 sessions of 2 trials per day) of aged rats supplemented for three months with MCT (FIG. 1A; P<0.007), PS -ω3 conjugate (FIG. 1B; P<0.07), SB-PS (FIG. 1C; P<0.02), LC-PUFA from fish oil (FIG. 1D; P<0.03) or fish oil+SB-PS mixture (FIG. 1E; P<0.11) was analyzed using video camera, with (open squares) or without (closed circuits) pretreatment of 1 mg/kg bodyweight of scopolamine. Values represent mean±S.E.M of four to five rats per supplement.

Figure 2:
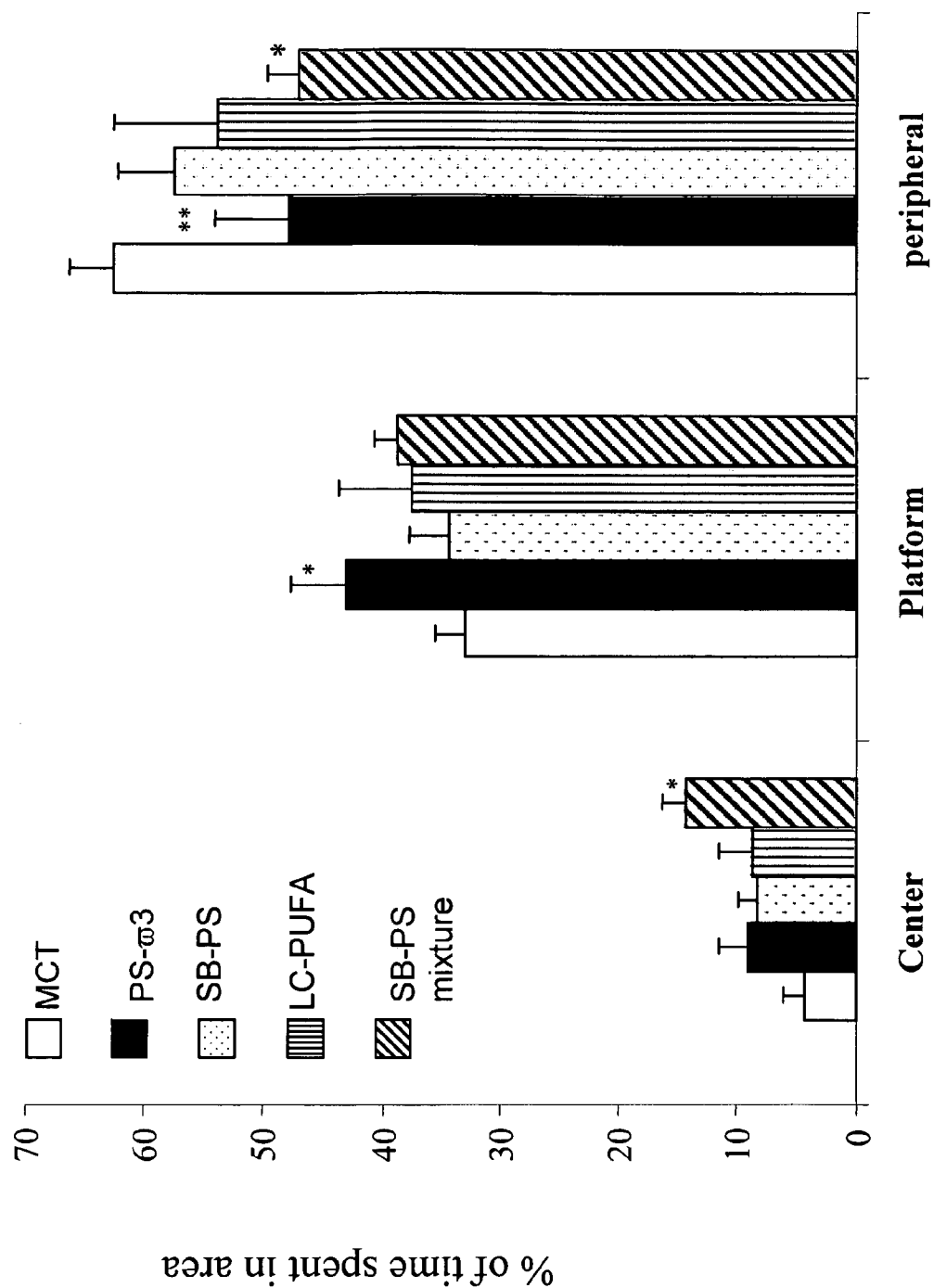
Figure 3:
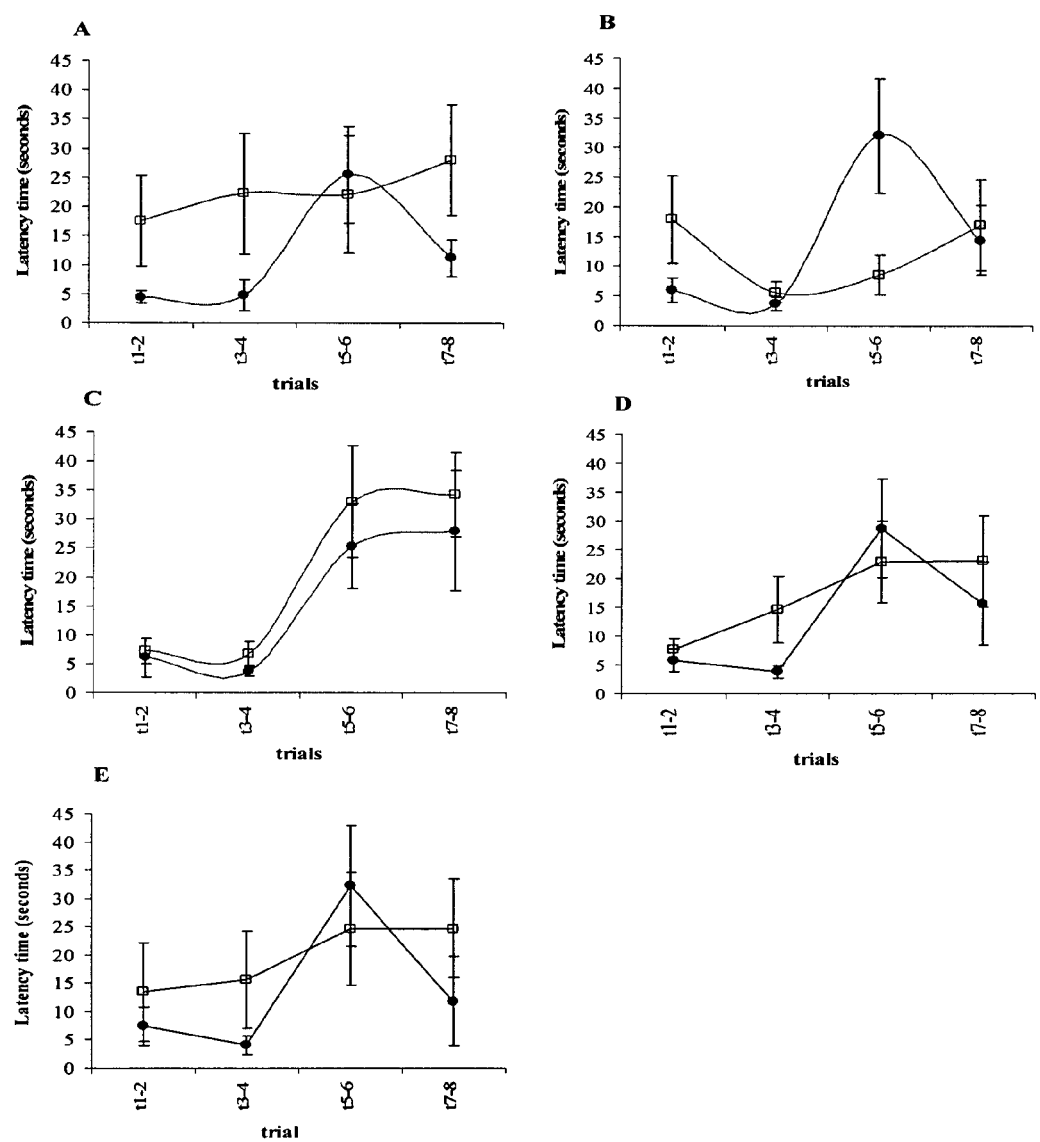

FIG. 2: Performance of scopolamine-treated rats in the Morris water maze task in the spatial probe test.

Percentage of latency time that aged rats, supplemented for three months with MCT (open bars), PS -ω3 conjugate (solid bars), SB-PS (dotted bars), LC-PUFA from fish oil (striped bars) or fish oil+SB-PS mixture (hatched bars), spent in different areas after the platform being removed, was analyzed using video camera, following pre-treatment of 1 mg/kg bodyweight of scopolamine. Values represent mean±S.E.M of four to five rats per supplement. Significance compared to control group (MCT)*P-value<0.05 and **P<0.08.

FIG. 3A-3E: Performance of scopolamine-induced rats in locating the platform after its reposition.

Latency time to platform on the fifth day of the water maze test, in which the platform was repositioned between the sessions, in aged rats supplemented for three months with MCT (FIG. 3A), PS -ω3 conjugate (FIG. 3B), SB-PS (FIG. 3C), LC-PUFA from fish oil (FIG. 3D) or fish oil+SB-PS mixture (FIG. 3E), was analyzed using video camera, with (open squares) or without (closed circuits) pretreatment of 1 mg/kg bodyweight of scopolamine. Values represent mean±S.E.M of four to five rats per supplement.

Figure 4:
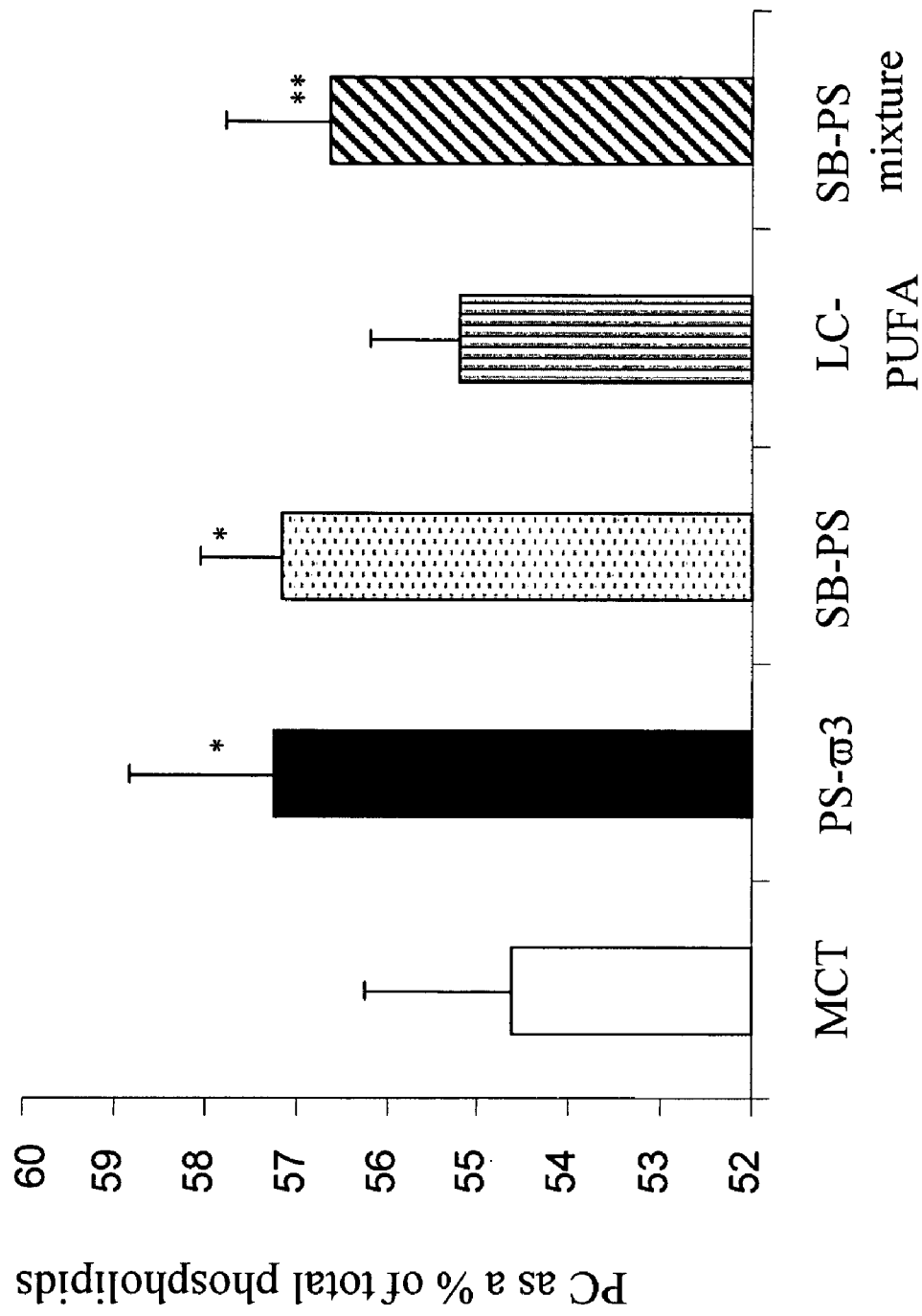

FIG. 4: Phospholipid levels in rat cortex as measured using $^{31}$P-NMR.

Lipids were extracted from liver tissues of aged rats that were supplemented for three months with MCT (open bars), PS -ω3 conjugate (solid bars), SB-PS (dotted bars) LC-PUFA from fish oil (striped bars) or fish oil+SB-PS mixture (hatched bars). Phospholipids levels were analyzed using a $^{31}$P-NMR machine and the relative levels of phosphatidylcholine of the different treatments are presented. Values represent mean±S.D. of four to five rat tissues per supplement. Significance compared to control group (MCT)*P<0.05 and **P<0.1.

Figure 5:
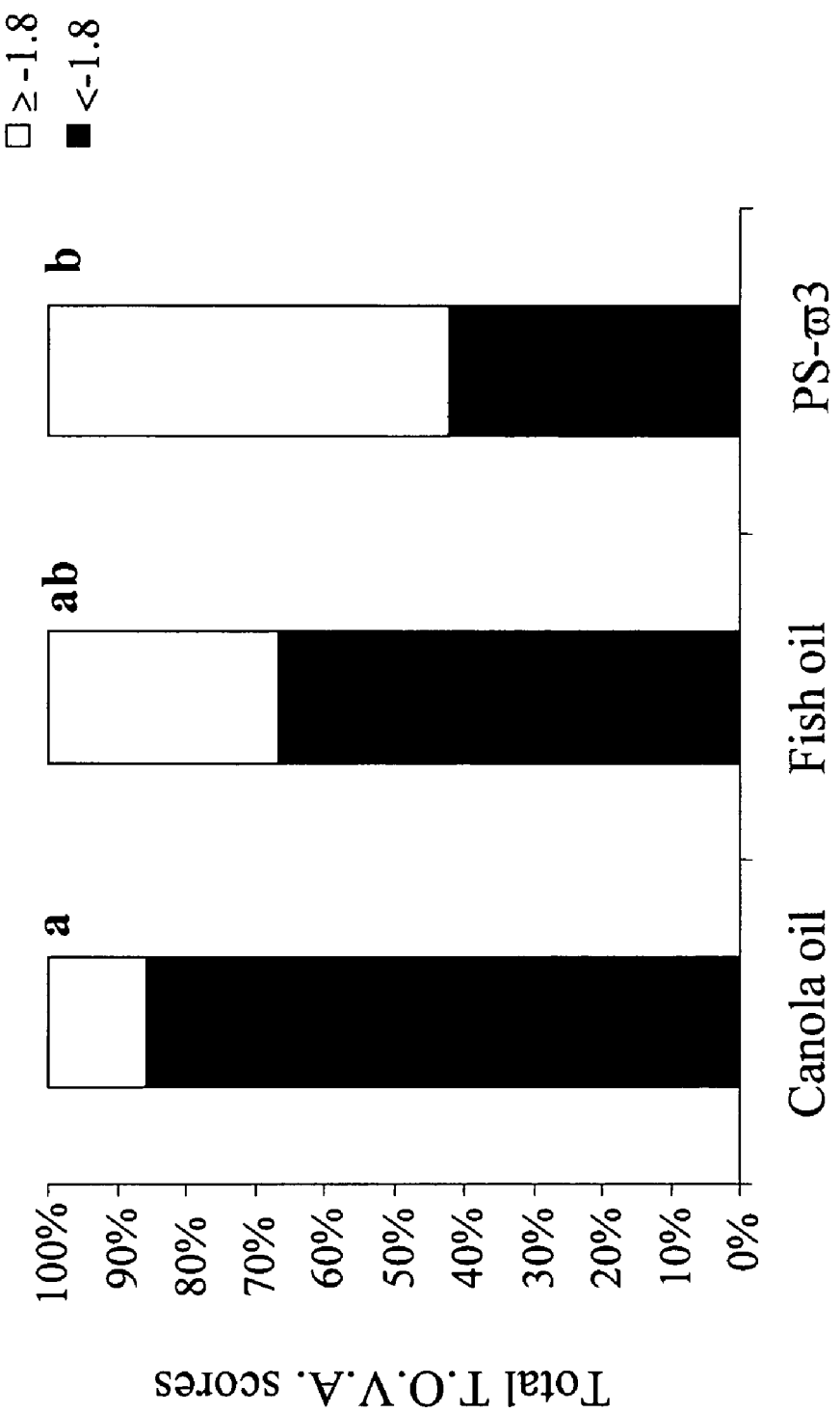

FIG. 5: Improvement of ADHD index score.

Total T.O.V.A. scores following the feeding phase are compared to the enrollment criteria of total score>1.8 standard deviations from age and sex adjusted normal means. Chi-square test was used to determine statistical differences between means of tested groups (P<0.015).

Figure 6:
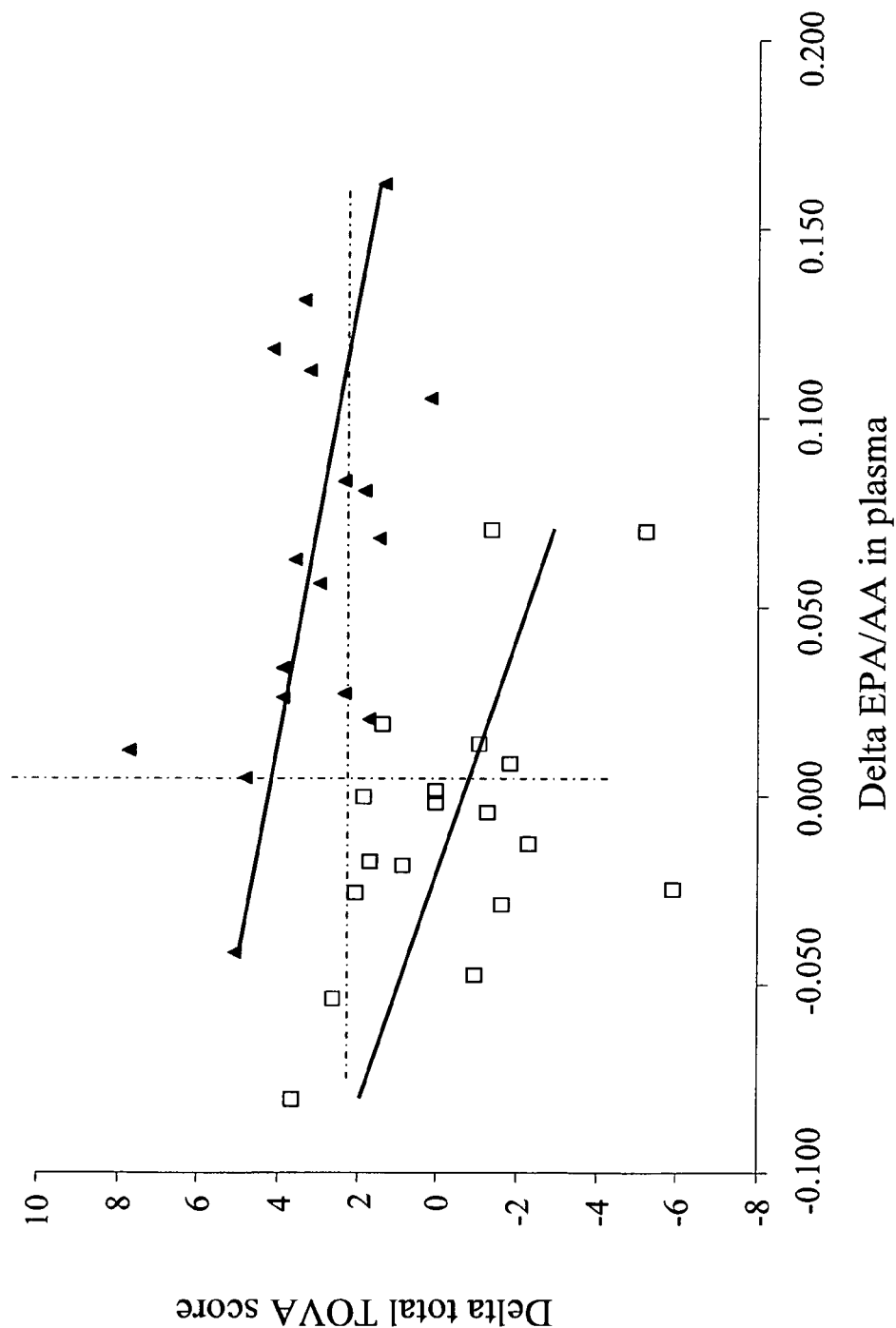

FIG. 6: Linear correlations between ΔEPA/ARA and ΔADHD index score in different treatments Changes in standardized total T.O.V.A. scores were correlated to changes in eicosapentaenoic levels following the feeding with canola oil (empty squares; r=−0.482, P<0.05) or PS -ω3 conjugate (black triangles; r=−0.517, P<0.05). Parallel correlation analysis of changes in the fish oil-fed subjects (data no shown; r=0.110, P<NS) demonstrated mixed trends of these treatments.

Figure 7:
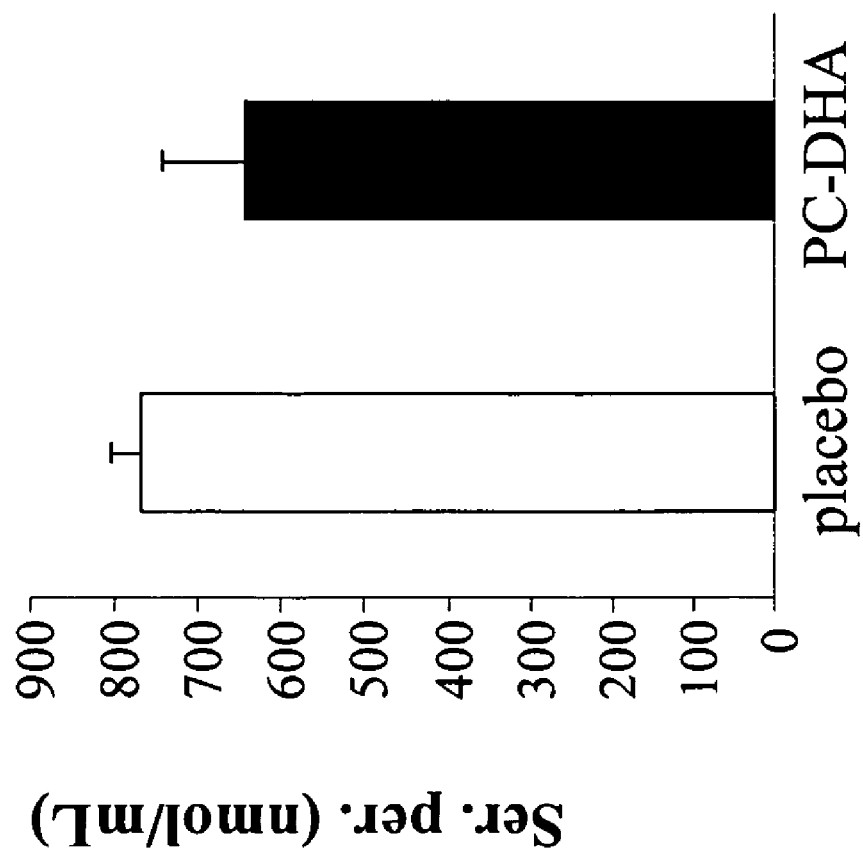

FIG. 7: Effect of PC-DHA on the serum oxidative stress.

Apo E° mice were fed for 10 weeks with placebo (open bars) or PC-DHA (solid bars). Serum lipid peroxide (Ser. per.) levels were measured using a spectrophotometric assay. Values represent mean±S.D. of 5 mice per treatment.

DETAILED DESCRIPTION OF THE INVENTION

In a first aspect the present invention provides a lipid preparation, wherein said lipid is a glycerophospholipid, a salt, conjugate, and derivative thereof, and any mixture thereof, and poly-unsaturated fatty acid (PUFA) acyl groups, particularly long-chain poly-unsaturated fatty acid (LC-PUFA) acyl groups, preferably omega-3 and/or omega-6 acyl groups, at a concentration of least 5% (w/w) of total fatty acids content of said preparation, preferably at least 8% (w/w), more preferably more than 10% (w/w), most preferably 20-50% (w/w), wherein said PUFA is covalently bound to said glycerophospholipid.

Preferably, said lipid is a glycerophospholipid in which at least some of the sn-1 or sn-2 groups of the glycerol backbone are substituted with said poly-unsaturated fatty acid (PUFA) acyl groups.

In one specific embodiment, said lipid is a mixture of glycerophospholipids of formula I:

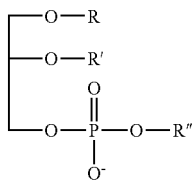

Formula (I)

wherein R" represents a moiety selected from serine (PS), choline (PC), ethanolamine (PE), inositol (PI), glycerol (PG) and hydrogen (phosphatidic acid—PA), and R and R', which may be identical or different, independently represent hydrogen or an acyl group, wherein said acyl group is selected from saturated, mono-unsaturated or poly-unsaturated acyl groups (PUFA), particularly long-chain poly-unsaturated fatty acids (LC-PUFA), more preferably omega-3 and/or omega-6 acyl groups, and salts thereof, with the proviso that R and R' cannot simultaneously represent hydrogen, and wherein said polyunsaturated acyl groups comprise at least 5% (w/w) of total lipid fatty acids, preferably more than 10% (w/w), and particularly 20-50% (w/w).

More specifically, in one most preferred embodiment, the present invention provides a lipid preparation, wherein said lipid is a mixture of glycerophospholipids comprising a glycerophospholipid of Formula I above, wherein R" represents a serine moiety, and R and R', which may be identical or different, independently represent hydrogen or an acyl group, wherein said acyl group is selected from saturated, mono-unsaturated or poly-unsaturated acyl groups (PUFA), particularly long-chain poly-unsaturated fatty acids (LC-PUFA), more preferably omega-3 and/or omega-6 acyl groups, and salts thereof, with the proviso that R and R' cannot simultaneously represent hydrogen, and wherein said LC-PUFA constitute at least 5% (w/w) of total fatty acids content of said preparation, preferably at least 8% (w/w), more preferably above 10% (w/w), and particularly 20-50% (w/w), said mixture optionally further comprising other glycerophospholipids, for use as an agent for the prevention, maintenance, improvement and/or treatment of cognitive and mental conditions in a subject in need, particularly mental and/or psychiatric disorders selected from the group consisting of Attention Deficit Disorder (ADD)/Attention Deficit Hyperactivity Disorder (ADHD), dyslexia, memory impairment and learning disorders, amnesia, mild cognitive impairment, cognitively impaired non-demented, pre-Alzheimer's disease, Alzheimer's disease, pre-dementia syndrome, dementia, age related cognitive decline, cognitive deterioration, moderate mental impairment, conditions that influence the intensity of brain waves and/or brain glucose utilization, stress, anxiety, child behavior disorders, concentration and attention impairment, mood deterioration, general cognitive and mental well being, neurodegenerative disorders, hormonal disorders, depression, Parkinson's disease, multiple sclerosis (MS), aging and cognitive decline.

In one more particular embodiment of said preparation, R represents hydrogen and R' represents an acyl group. Alternatively, R' represents hydrogen and R represents an acyl group.

Considering these latter embodiments, when said acyl group is preferably an omega-3 acyl group, it may be an eicosapentaenoyl, a docosahexaenoyl group, or linolenic omega-3 group. And, when said acyl group is preferably an omega-6 acyl group, it may be an arachidonoyl group, or a linoleic omega-6 group. A further possibility is that said acyl group may be a linolenoyl (18:3) group.

In a further particular embodiment, the identity and content of R and R' are predetermined.

In another particular embodiment, said gycerophospholipid substantially mimics the fatty acid composition and/or fatty acid profile of human or mammalian brain phosphatidylserine (PS). Preferably, said mixture of glycerophospholipids comprises at least 10% (w/w) PS, more preferably at least 15% (w/w), even more preferably at least 20% (w/w), most preferably 25% (w/w). Alternatively, said mixture of glycerophospholipids comprises at least 40% (w/w) PS, more preferably at least 50% (w/w), even more preferably at least 60% (w/w), most preferably 70% (w/w).

Nonetheless, the invention also refers to preparations which are different from human brain PS, but still have an improved bioactivity, particularly as compared to soybean-PS. Said improved bioactivity was particularly evidenced by the results presented in Examples 1 and 2.

Traditionally, PS active ingredients used as dietary supplements were produced from animal brain extracts, particularly bovine brain. The PS extracted from animal brain tissues, similarly to human brain PS, has a fatty acid composition which is characterized by relatively higher levels of omega-3 moieties, compared to the levels of omega-3 found in plant phospholipids.

PS has the following structure:

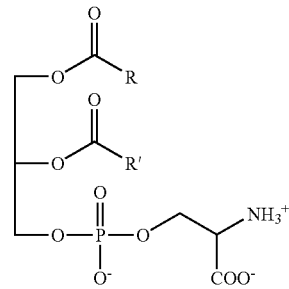

Formula II

Human brain PS is characterized by over 20-30% PS containing omega-3 fatty acyls, preferably at the sn-2 position of the glycerol moiety, and mainly DHA or EPA. As mentioned above, phospholipids, and PS in particular, are responsible for membrane structure and physical properties. One of the major physical properties governed by phospholipids is the fluidity of these membranes. Omega-3 fatty acids, DHA and EPA in particular, also have a crucial role in membrane fluidity in light of their unique 3D structure. Therefore, PS with omega-3 fatty acyl moieties, DHA and EPA in particular, has unique bio-functionality which cannot stem from just the basic phospholipid skeleton of this phospholipid.

It was the bovine brain cortex PS (BC-PS) that Toffano and Bruni reported in the early 1980's to be a pharmacologically active compound, which counteracts age-related changes in the central nervous system [Toffano et al. (1980) *Pharmacol. Res. Commun.* 12:829-845]. The fatty acid analysis of this PS extract indicated that the main molecular species are 1-octadecanoyl-2-docosahexaenoyl-sn-glycero-3-phosphorylserine and 1-octadecanoyl-2-octadecenoyl-sn-glycero-3-phosphorylserine. The major fatty acids profile detected in the various PS preparations (whole brain, white matter and gray matter) were stearic acid (18:0; 37.6-41.6%), oleic acid (18:1 ω9; 15.3-37.6%), adrenic acid (22:4 ω6; 3.8-7.6%) and DHA (7.6-28.7%). In animal studies, BC-PS has been shown to affect multiple neurochemical systems, neuronal membranes, cell metabolism, and neurotransmitter systems including acetylcholine, norepinephrine, serotonin and dopamine [McDaniel et al. (2003) *Nutrition.* 19:957-975]. In human, age-associated memory impairment patients treated with BC-PS, had improved performance tests related to learning and memory tasks of daily life. In geriatric patients, BC-PS significantly improved behavioral and cognitive parameters [McDaniel et al. (2003) id ibid]. Importantly, the results of a multi-center, double-blind, placebo-controlled trial with Alzheimer's disease patients, suggested that BC-PS improve cognitive performance, especially in patients with severe cognitive impairment [McDaniel et al. (2003) id ibid]. Conversely, another study in Alzheimer's disease patients suggests that the most apparent differences between the treatment groups are among patients with less severe cognitive impairment [McDaniel et al. (2003) *id ibid]*.

Considering the risks involved with prion diseases, particularly bovine spongiform encephalopathy (BSE), as well as other disadvantages associated with ingredients obtained from animal sources, PS supplements are often prepared using PS originating from soybean lecithin (also known as soybean-PS). This lecithin is enriched, usually enzymatically, with PS. This method of production results in PS with a fatty acid profile of soybean phospholipids, which is characterized by low level of omega-3 fatty acids, and almost no DHA and EPA, and thus, not so effective in delivering these fatty acids.

The US-FDA has noted that the fatty acid composition of PS derived from bovine brain and soy lecithin differs in their fatty acids. PS from soy lecithin contains mainly poly-unsaturated fatty acids (PUFA) like linoleic, while PS derived from bovine brain contains mainly saturated and monounsaturated fatty acids, as well as some long-chain-PUFA (LC-PUFA) like DHA. Additionally, the relative proportions of fatty acids from the omega-3 and omega-6 series vary in the PS molecules from bovine and soy products. In fact, the PS molecule from soy has 7% alpha-linolenic acid (omega-3) and 47% linoleic acid (omega-6), while the PS molecule derived from bovine brain cortex has 8% DHA (omega-3) and 2% ARA (omega-6) [published at http://www.cfsan.fda.gov/~dms/ds-ltr36.html]. The FDA has therefore concluded that the different fatty acids differ in their metabolism, biological activity, and potency. Thus, the PS molecules from bovine brain cortex and soy lecithin differ significantly in their fatty acid composition, and they are not the same substance.

Moreover, the bio-functionality of soybean-PS (SB-PS) in the improvement of cognitive function is also different from (and poorer than) human brain PS [*Jorissen et al.* (2001) *Nutr. Neurosci.* 4:121-134].

Thus, it is a purpose of the present invention to provide a PS preparation with a predetermined fatty acid composition that mimics the fatty acid composition of human brain PS, having a fatty-acid profile which is equivalent to that of human brain PS, and which is more efficient than SB-PS in delivering omega-3 fatty acids to the brain.

The PS preparation provided herein, while not identical to naturally occurring brain PS, is characterized by improved functionality, particularly in comparison with soybean-PS, as shown in the Examples below.

The PS preparation of the present invention is enriched with omega-3 fatty acyls, preferably DHA, EPA or linolenic omega-3. Furthermore, the PS of this invention is enriched with omega-3 fatty acyls covalently bonded to either or both of the sn-1 or sn-2 positions of the glycerol moiety in the PS backbone.

The present invention is also related and describes other phospholipids, such as phosphatidylcholine (PC), phosphatidylethanolamine (PE), phosphatidyl-inositol (PI), phosphatidylglycerol (PG) and phosphatidic acid (PA), enriched with omega-3 fatty acids, preferably DHA, EPA, or linolenic acid which are covalently bonded at either or both of the sn-1 or sn-2 positions of the glycerol moiety of the phospholipid. Alternatively, the phospholipids of the invention are enriched with omega-6 fatty acids. Thus, in an additional embodiment, R" may be any one of serine, choline, ethanolamine, inositol or glycerol.

When referring to PS in the present description, it should be taken to mean also any other lipid, such as, but not limited to, the polar lipids listed above.

In a preferred embodiment, the amount of omega-3 (particularly EPA, DHA or linolenic acid) or omega-6 (particularly ARA and linoleic acid) fatty acids in the PS preparation of the invention is greater than 7% at either or both of the sn-1 or sn-2 positions, preferably at the sn-2 position, preferably over 10%, more preferably over 20% and most preferably above 40%.

As mentioned, the desired omega-3/omega-6 fatty acyls can be bonded at both or only one of the sn-1 and sn-2 positions.

In yet another preferred embodiment, the level of EPA fatty acids in the PS preparation of the invention is higher than the level of DHA fatty acids. Alternatively, the ratio between EPA and DHA fatty acids in the PS preparation of the invention can range from about 10:1 to 1:10, preferably from 5:1 to 1:5, more preferably from 3:1 to 1:3. A most preferred ratio of EPA and DHA is between 1.5:1 to 1:1.5. In yet a further embodiment, the PS preparation of the invention contains low levels of EPA fatty acids, preferably less than 10% (w/w) of total fatty acids content of said preparation, more preferably less than 5% (w/w), even more preferably less than 1% (w/w), most preferably less than 0.5% (w/w).

The fatty acid composition of the PS preparation of the present invention can have a predetermined fatty acid composition similar to or different from the fatty acid composition found in normal healthy human brain, provided it has enhanced activity, particularly compared to the activity of plant PS, for example soybean-PS.

By the term "enhanced activity" (or "enhanced bioactivity", or "enhanced bioavailability", "improved bioactivity", or "improved bioavailability") it is understood the ability to e.g., increase the levels of LC-PUFA in the tissues of a subject who consumes (ingests or is administered with it) the preparation of the invention. Alternatively, said enhanced activity is measured by methods which evaluate the cognitive capabilities of said subject.

The preparation of the omega-3/omega-6-enriched PS preparation of the present invention is through enzymatic, chemical or molecular biology methods. Briefly, PS can be enriched with omega-3 or omega-6 moieties by enzymatic processes, e.g. enrichment of a natural phospholipid/lecithin with omega-3 fatty acids by enzymatic transesterification/esterification followed by transformation of the head group to serine (using PLD enzymes) to obtain a PS-omega-3/omega-6 conjugate. Another enzymatic pathway is to obtain a marine-derived lecithin or phospholipid source which is naturally rich in omega-3 acids, such as krill, fish or algae phospholipids, and transform their head groups to serine, as exemplified in Example 1 below. It is to be noted that the fatty acid composition of the PS obtained by this method has an omega-3 composition which is predetermined by the source of choice (fish, krill, algae, etc.) (see Table 1 below). Such methods have been thoroughly described in WO 2005/038037.

The PS-omega-3/omega-6 preparation of the present invention can also be prepared by chemical transesterification/esterification methods that will enrich the sn-1 and 2 positions with omega-3 or omega-6 acyl residues. Such methods of preparation of PS-omega-3 and PS-omega-6 have been described in WO 2005/038037.

Alternatively, the PS preparation of the present invention can be prepared by GMO (genetically modified organisms)/biotechnology methods, for example, providing phospholipids-producing organisms with omega-3 or omega-6 fatty acids to obtain phospholipids enriched with omega-3 or omega-6 PS. It may be preferred to use genetically engineered plants or microorganisms, to avoid use of animal sources.

The PS of the present invention can have the omega-3 or omega-6 fatty acid composition of a specific lecithin raw material, relatively rich with omega-3 or omega-6 fatty acids, enriched with PS to yield a PS preparation with elevated omega-3 or omega-6 fatty acids levels, compared to soybean-PS. Such is the case, for example, when phospholipids from krill are used as the starting material, as described above.

In a preferred embodiment the PS enriched with omega-3 or omega-6 can be soybean-PS or any other PS, from plant, animal, for example krill, or microorganism source. In a further preferred embodiment the omega-3 or omega-6 enrichment can be performed on a lecithin, which in turn is enriched with PS by transphosphatidylation.

It is the purpose of this invention to provide a novel PS preparation, enriched with omega-3 fatty acids, resulting in a preparation with improved efficacy compared to preparations containing natural or simply enriched PS.

The improved PS preparation of the present invention exhibits enhanced activity in the improvement and treatment of cognitive and mental conditions and disorders as well as the maintenance of normal functions of brain related systems and processes. These include, but are not limited to ADHD, multiple sclerosis (MS), dyslexia, depression, learning capabilities, intensity of brain waves, stress, mental and psychiatric disorders, neurological disorders, hormonal disorders, concentration and attention, mood, brain glucose utilization, and general cognitive and mental well being. The results presented in Example 3 below, regarding the dietary supplementation of ADHD children with a PS-$\bar{\omega}$3 preparation further demonstrate its enhanced activity and properties in the improvement of this cognitive condition.

Thus, the preparation of the invention is suitable for the prevention, maintenance, improvement and/or treatment of cognitive and mental conditions in children, particularly mental and/or psychiatric disorders selected from the group consisting of Attention Deficit Disorder (ADD)/Attention Deficit Hyperactivity Disorder (ADHD), dyslexia, memory impairment and learning disorders, conditions that influence the intensity of brain waves and/or brain glucose utilization, stress, anxiety, child behavior disorders, concentration and attention impairment, mood deterioration, general cognitive and mental well being, neurodegenerative disorders and hormonal disorders.

The preparation of the invention is also suitable for the prevention, maintenance, improvement and/or treatment of cognitive and mental conditions in adults, particularly mental and psychiatric disorders selected from the group consisting of Attention Deficit Disorder (ADD)/Attention Deficit Hyperactivity Disorder (ADHD), age-associated memory impairment and learning disorders especially in the elderly, amnesia, mild cognitive impairment, cognitively impaired non-demented, pre-Alzheimer's disease, Alzheimer's disease, pre-dementia syndrome, dementia, age related cognitive decline, cognitive deterioration, moderate mental impairment, depression, Parkinson's disease, multiple sclerosis (MS), dyslexia, aging, cognitive decline, conditions that influence the intensity of brain waves and/or brain glucose utilization, stress, anxiety, concentration and attention impairment, mood deterioration, cognitive decline, neurodegenerative disorders and hormonal disorders.

Hence, the present invention also provides a method of treatment for any of the above-mentioned conditions, said method comprising administering a therapeutically effective dosage of the lipid preparation of the invention to a subject in need. As specified below, the lipid preparation of the invention may be administered per se, or comprised in a pharmaceutical composition, a dietary supplement, a food article, a nutraceutical product, or any other suitable form.

The terms "effective dosage", "effective amount" or "sufficient amount" mean an amount necessary to achieve a selected result, which at present, involves the amount of lipid preparation of the invention necessary for e.g. increasing the levels of LC-PUFA in the tissues (at least one) of the subject in need, or improving the subject's performance in a cognitive test. Usually, a "therapeutically effective amount" is determined by the severity of the disease in conjunction with the preventive or therapeutic objectives, the route of administration and the patient's general condition (age, sex, weight and other considerations known to the attending physician). The decision as to the particular dosage to be employed (and the number of times to be administered per day) is within the discretion of the physician, and may be varied by titration of the dosage to the particular circumstances of this invention to produce the desired therapeutic effect.

The novel lipid preparation of the present invention exhibits enhanced activity in the improvement of cognitive functions, as detailed hereunder, over omega-3 or omega-6 lipids per se or soybean-PS. Furthermore, under certain conditions or for all or specific disorders, the lipid preparation of the invention is effective at a dosage of less than 100 mg/day of PS. This is lower than the current recommended daily dosage of soybean-PS (100-300 mg/day) or omega-3 lipids (approx. 0.1-2 g/day or more) currently available in the market. Nonetheless, dosages of 100-600 mg/day are preferred for enhanced efficacy of the lipid preparation of the present invention.

An important advantage of the PS preparation of the invention is that it exhibits multifunctional activity. This multi-functionality is exhibited by improvement in cognitive and mental functions, together with improvement of other health disorders or conditions.

The enhanced activity of this PS preparation, as well as its multi-functionality, may arise from the unique structure of this preparation and its influence on the physical and chemical properties of cell membranes in brain tissues as well as other organs and tissues.

The enhanced activity of this PS preparation, as well as its multi-functionality, may also be attributed to the enhanced bioavailability of the omega-3 fatty acids, due to their incorporation in the PS skeleton. Thus, the omega-3 fatty acids may be delivered to the brain across the blood-brain barrier, being part of the PS molecule, which readily passes this barrier. The PS functions as a delivery platform for the fatty acids bound thereto, to various organs and tissues, thereby enhancing their bioavailability.

Additional health disorders or conditions which may be treated or improved by the multifunctional PS preparation of the invention include, but are not limited to high blood cholesterol levels, high triglycerides levels, high blood fibrinogen levels, HDL/LDL ratio, diabetes, metabolic syndrome, menopausal or post-menopausal conditions, hormone related disorders, vision disorders, inflammatory disorders, immune disorders, liver diseases, chronic hepatitis, steatosis, phospholipid deficiency, lipid peroxidation, dysrhythmia of cell regeneration, destabilization of cell membranes, coronary artery disease, high blood pressure, cancer, hypertension, aging, kidney disease, skin diseases, edema, gastrointestinal diseases, peripheral vascular system diseases, allergies, airways diseases, neurodegenerative and psychiatric diseases.

The lipid preparations of the invention may be delivered per se, or comprised in dietary supplements, functional food articles, nutraceutical products, pharmaceutical compositions, etc.

The preparation of pharmaceutical compositions is well known in the art and has been described in many articles and textbooks, see e.g., Gennaro A. R. ed. (1990) *Remington's Pharmaceutical Sciences*, Mack Publishing Company, Easton, Pa., and especially pages 1521-1712 therein.

Dietary supplements comprising the preparation of the invention may be delivered in the form of soft gel capsules, tablets, syrups, and any other common dietary supplements delivery systems.

Functional food articles comprising the preparation of the invention are any one of dairy products, ice-creams, biscuits, soy products, pastries, cakes and breads, instant foods, frozen foods, prepared foods, instant products, sauces, condiments, oils and fats, margarines, spreads, fillings, cereals, drinks and shakes, infant formulas, infant foods (biscuits, mashed vegetables and fruits, cereals), bars, snacks, candies, chocolate products and confectionary.

The term "infant formula" as used herein encompasses infant formulas (for newborn to 6 months old infants), follow-up formulas (for 6-12 months old babies) and growing up formulas (for 1-3 years old children).

Pharmaceutical compositions comprising the preparation of the invention may be delivered orally, intravenously, or by any other conventional or special route of administration, particularly tablets, capsules, pellets, solutions, suspensions, elixirs, injections and patches.

The preparation of the invention may be in the form of fluid oil, powder, granules, wax, paste, oil or aqueous emulsion, and any other form that will enable its use in the target applications.

Pharmaceutical or nutraceutical formulations comprising the PS preparation of the invention may further include physiologically acceptable free flowing agents, other additives, excipients, dessicants, edible fibers and diluents, colorants, aroma and taste ingredients, and any ingredients that control physical, organoleptic, and other properties, as well as additional active ingredients, for example minerals, vitamins, other nutritional additives.

Often, the utilization of omega-3 lipids in a variety of applications, and especially as ingredient of functional foods, is hindered due to their distinct fish odor. Thus, another advantage of the omega-3 enriched phospholipids preparations of the present invention is that they have reduced odor or taste of omega-3 acyl moieties, due to the covalent binding of these groups to the PS backbone, as shown in Example 5. This increases the vapor pressure of these materials, hence reducing their distinct aroma. Thus, the covalent binding of the omega-3 fatty acids to the phospholipid backbone, especially PS, alters and improves their taste properties.

Furthermore, the PS preparation of the invention demonstrated enhanced stability with regards to the oxidation sensitive omega-3 fatty acids. Phospholipids in general, and PS in particular, are known to act as anti-oxidants and stabilizers.

These benefits make the lipid preparation of the invention highly beneficial and important in a variety of applications and especially in functional foods, where stability, aroma and taste are fundamental requirements.

In addition, the preparation of the invention can be formulated with additional lipids for an even more enhanced bio-functionality and efficacy.

The polar lipids derivatives of PUFA, such as the PS-PUFA derivatives have exhibited high stability as a preparation and additionally in several food applications, used in the clinical trials of the present invention. The stability of these sensitive compounds is emerging from the covalent combination of phospholipids, known in the past to be used as preservatives and of the un-stable PUFA moieties.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example 1

Preparation of PS-$\bar{\omega}$3 Conjugate from Three Different Marine Lecithin Sources and Incorporation of PS-$\bar{\omega}$3 Conjugate to Food Product Lecithin from three different marine sources was subjected to transphosphatidylation in the presence of phospholipase D (PLD) and L-serine. Following the reaction, the preparation was purified from most of the neutral lipids, and analyzed in order to determine percentage of PS, EPA and DHA (Table 1).

As demonstrated in Table 1, the ratio between EPA and DHA fatty acids of the different PS preparations varies as a function of the marine source. PS-$\bar{\omega}$3 conjugate preparation of marine source lecithin 1 and of marine source lecithin 2, exhibit higher level of EPA than DHA, while PS-$\bar{\omega}$3 conjugate preparation of marine source lecithin 3 has lower level of EPA than DHA (see Table 1).

TABLE 1

| | % w/w of PS in the product | % w/w from total product | | | % w/w from PS fatty acids | | |
|---|---|---|---|---|---|---|---|
| | | EPA | DHA | Ratio EPA:DHA | EPA | DHA | Ratio EPA:DHA |
| PS-ω3 conjugate preparation of marine source lecithin 1 | 20 | 10.5 | 6.5 | 1.6:1 | 35 | 17 | 2:1 |
| PS-ω3 conjugate preparation of marine source lecithin 2 | 50 | 16.8 | 5.85 | 2.9:1 | 31.6 | 10.5 | 3:1 |
| PS-ω3 conjugate preparation of marine source lecithin 3 | 48 | 3.8 | 13.5 | 1:3.5 | 11 | 32 | 1:2.9 |

Preparation of the PS-ω3 Conjugate Chocolate Spread

PS-ω3 conjugate preparation of marine source lecithin 1 was mixed with anti-oxidants and oil-based fruit taste and fragrance extracts. 1.5 g of this preparation was mixed into 24 g of chocolate spread (Chocolate spread "HaShachar", HaShachar HaOle, Haifa, Israel) and was packed separately. This amount was adjustable according to the described daily dosage (250 mg/d EPA+DHA and 300 mg/d PS), and was generally taken on a single slice of bread.

Example 2

Efficacy of Dietary EPA/DHA Esterified to Triglyceride or Phosphatidylserine to Attenuate Scopolamine-Induced Amnesia and to Serve as Substrate for Cerebral Cortices DHA Accretion in an Elderly Rat Model Methods
Animals and Diet Male Wistar rats originated from the same colonies were obtained from Harlan (Harlan Laboratories Limited, Jerusalem, Israel). All rats were housed in a standard environment, in which temperature was maintained at 24±0.5° C., and the relative humidity was kept at 65±5% with 12-h periods of light and dark. Body weight was measured at the beginning and the end of the treatment period. Hundred rats were randomly divided into five dietary supplemented groups, in addition to their normal diet five groups received, 100 mg of the followings, incorporated to 1 ml of milk-based supplement matrix: (i) MCT (MCT group); (ii) fish oil diluted with MCT to give 30% (w/w) of omega-3 LC-PUFA (also referred to as LC-PUFA or fish oil group); (iii) of soybean 78% powdered soy lecithin transphosphatidylated PS (final concentration of 20% SB-PS (w/w)) emulsified with lecithin and further diluted with MCT (SB-PS group); (iv) fish oil mixed with soybean 78% powdered soy lecithin transphosphatidylated PS and diluted with MCT to give final concentration of 20% SB-PS (w/w) and 30% (w/w) of omega-3 LC-PUFA, wherein the level of DHA is lower than the level of EPA (fish oil+SB-PS mixture group) and (v) 20% PS (w/w) consisting largely of molecular species of palmitic acid (16:0), DHA and EPA, resulting with all in all 30% (w/w) of omega-3 LC-PUFA, wherein the level of DHA is lower than the level of EPA (PS-ω3 conjugate group). The supplement matrices were stored at −20° C., and fresh portions were daily administered to the rats individually per os using 1 ml disposable sterile syringes. All supplements were handled so as to minimize oxidation of the fatty acids. Rats consumed the normal chow and water ad libitum as well as the aforementioned supplementation.

Behavioral Testing

Water maze test, which was developed by Morris [Stewart, C A. and Morris, R G. (1993) The water maze. In: *Behavioural Neuroscience: A Practical Approach*. Vol. 1, Saghal, A. ed., pp. 107-122, Oxford University Press, New York, N.Y.], uses a circular tank (137 cm diameter, 35 cm deep) constructed of opaque white plastic. It is filled with water (21-22° C.) to a depth of 28 cm, and the water is rendered opaque by the addition of soluble, nontoxic black latex paint. In the place version of the maze, the rat develops a spatial map of the extra-maze cues, which it then uses to locate the platform. Thus the distance swum to the platform and the time taken in doing so should decrease over testing sessions (days) as the rat learns the location of the platform. Moreover, it is expected that if the rat has learned the location of the platform in relation to the extramaze cues, its initial response on the probe trial will be to swim directly to the quadrant in which it expects to find the platform. Thus the distance swum (and time spent) in the target quadrant should be greater than that in the other two quadrants (excluding the start quadrant). The distance swum to the platform, as well as the latency to reach the platform were monitored using the video-based tracking system. The behavioral testing was conducted during the dark cycle, when rats are normally most active. The pool was located in a test room in which there were many extra-maze spatial cues. On the first three days, the rats were required to locate the hidden platform (15.5 cm×15.5 cm) situated 1 cm below the surface of the water. There were two acquisition testing sessions per day, with four trials per session. On each trial, the rat was placed, facing the wall, in one of the four quadrants in the tank, and allowed to swim for a maximum of 60 seconds. Once the rat found the platform, it remained there for 5 seconds before being returned to the holding cage, which was kept warm on a heating pad. If the rat failed to find the platform in that time, it was placed on it for 5 seconds before being returned to the holding cage. Each of the eight trials conducted each day was started from a different quadrant, with the order determined pseudo-randomly (not twice from the same quadrant) and varying from day to day. The inter-trial interval (ITI) was 120 seconds, counted from the end of one trial to the beginning of the next. On fourth day, followed by a session as abovementioned, the platform was removed from the tank, and a probe trial was conducted by placing the rat in the quadrant opposite to that of the platform and then allowing it to swim for 60 seconds. The day following the probe trial, the rats were tested with a session in which the maze was set up as previously described, followed by a session in which the platform was repositioned to the center of the opposite quadrant. The latency to find the platform on each trial was recorded. Scopolamine (1 mg/Kg) was intraperitoneally (i.p.) administered 30 minutes before the indicated trials.

Lipid Extraction and NMR Analyses

At the end of the behavioral testing, the rats were anesthetized with Halothane and then decapitated. Liver and brain tissues were quickly removed and stored (at −80° C.). The lipid fraction of the rat tissues were extracted using a modified version of the technique described by Bligh and Dyer. Briefly, 500-700 mg and 300-1200 mg of liver and brain tissues, respectively, were homogenized in a solution of $CDCl_3$, methanol and CS-EDTA (1:2:2 v:v:v). The homogenates were further agitated using ultrasonic bath (10 min, 80° C.), followed by additional vigorous shaking (20 min). The relative ratio of the phospholipids in the homogenates was measured using high-resolution $^{31}$P-NMR at 121.MHZ using a 7.06 Tesla General Electric spectrometer.

These homogenates were further analyzed for their fatty acids distribution. First, the lipids extracts were desalted by reverse-phase chromatography using an RP-18 column; diheptadecanoyl phosphatidylcholine was added as internal standard before the loading on the column. Phospholipids were separated from neutral lipids, such as cholesterol, on silica gel plates (Merck 60) developed in isohexane: ether: formic acid 80:20:2 (v:v:v). The phospholipids spot was visualized by spraying primulin solution and compared with authentic phospholipids standards. Henicasonoic methyl ester (C21:0) was added as a 2nd internal standard and the phospholipids were converted to methyl esters by mild acid hydrolysis with 1% methanolic $H_2SO_4$ overnight at 50° C. The fatty acids profile of the different samples was determined by gas-liquid chromatography.

Results

Rat diet was supplemented with the indicated treatments for three months before performing the maze tasks. At the acquisition stage there was marked increase in the latency time to find the platform after the administration of scopolamine (1 mg/Kg) in the placebo group (P-value<0.0007; see FIG. 1A), which was demonstrated by previous publications. Comparing the learning curves of PS-ω3 conjugate treated rats with or without scopolamine induction was shown to be statistically insignificant (P-value<0.07; see FIG. 1B) suggesting that this supplement countered scopolamine deleterious effects. Interestingly, learning curves of rats fed with SB-PS or fish oil were less affected by scopolamine, with respect to the parallel MCT-fed performance; however the difference between these learning curves were still found to be statistically significant (P-value=0.023 and 0.025, respectively; see FIG. 1C-1D); while their mixture, i.e. fish oil+SB-PS mixture treated rats demonstrated a scopolamine-insensitivity that was comparable to PS-ω3 conjugate (P-Value=0.11; see FIG. 1E). Having all treated rats learn the task at a different rate, is in contradiction to data presented by Blokland et al. [Blokland et al. (1999) *Nutrition* 15(10): 778-83], which showed no difference between PS obtained from different sources and the empty vehicle, in a water maze test. However in this study the mice were fed with comparable amounts of PS (15 mg/Kg weight as oppose to 20 mg/Kg weight) that were injected intraperitoneally.

In the Morris water maze spatial probe task, rats treated with PS-ω3 conjugate showed a distinctively higher tendency than MCT-treated ones (P<0.085) for latency time at the zone where the platform was located during the acquisition task (FIG. 2); suggesting a superior spatial memory. None of the other supplementations, including the physical mixture of fish oil and SB-PS, i.e. fish oil+SB-PS mixture (P<0.15), were able to demonstrate similar effect. It is interesting to compare this remarkable learning and memory performance of PS-ω3 conjugate fed rats to what was previously reported for older rats under SB-PS administration [Suzuki et al (2001) id ibid.]. The percent of time spent by PS-ω3 conjugate treated rats at this study and by SB-PS treated old rats at Suzuki et al. in the platform quadrant is similar (~45%). However, though both supplements were orally administered, the PS dosage which was provided in the current study was one third of the levels used by Suzuki et al (20 mg/kg vs. 60 mg/kg, respectively). Indeed, SB-PS (20 mg/kg) treatment in elderly rats resulted in no significant learning or memory effect, compared with placebo (FIG. 2).

SB-PS and fish oil supplementation were previously shown to ameliorate stress and anxiety behavior in animal models and in students [Benton et al. (2001) *Nutr Neurosci;* 4:169-78; Hamazaki et al. (1999) *Lipids;* 34:S33-7]. As shown on FIG. 2, PS-ω3 conjugate treated rats presented a reduced tendency (P<0.08) to swim in the periphery zone, but rather demonstrated elevated latency time at the platform and central zones, suggesting reduced anxiety. These observations were not obtained for either SB-PS or fish oil treatments (see FIG. 2), but for fish oil+SB-PS mixture-fed rats; however the changes were limited to the peripheral and central zones. These findings could be further correlated with higher adventurous characteristics as evaluated by tasks like open field. Blokland et al. [Blokland et al. (1999) id ibid.] reported that BC-PS treated mice demonstrated a nonsignificant but clear tendency to be less adventurous in the open field behavior trial, by spending less time in the center area.

Finally, the most prominent and outstanding observation was the different learning performance that cholinergic-impaired rats demonstrated in response to the repositioning of the platform. As expected, under scopolamine sedation MCT-treated rats latency to platform before ($t_{1-2}$; $t_{3-4}$) and following ($t_{7-8}$) the repositioning was significantly elevated (P-value=0.03, 0.004 and 0.02, respectively; see FIG. 3A). At the first session, rats supplemented with fish oil, SB-PS or fish oil+SB-PS mixture displayed a similar latency time to platform, with or without scopolamine-induced effect, at start ($t_{1-2}$), but then ($t_{3-4}$) presented increased levels (P-value=0.33, 0.13, 0.18; 0.05, 0.01, 0.04, respectively; see FIGS. 3C-3E). Comparing scopolamine treated rats with the latency obtained by MCT-fed rats, it was shown that only SB-PS attenuate it amnesia-induces effect (P-value=0.045, 0.002), while feeding with fish oil showed only mild tendency (P-value=0.06, 0.13) and there was no notable effect for fish oil+SB-PS mixture supplementation (P-value=0.31, 0.20). Following the repositioning of platform, all scopolamine treated rats, fed with either fish oil, SB-PS or fish oil+SB-PS mixture demonstrated a comparable latency time to that obtained by MCT-fed rats (P-value=0.25, 0.5 and 0.4).

In the PS-ω3 conjugate treatment (FIG. 3B), latency time was elevated following scopolamine administration at the first session, similarly to what was observed in either MCT or (P-value=0.48) fish oil+SB-PS mixture treatments, but then these rats presented a highly significant reduced latency levels when compared to MCT (P-value=0.004) or non-scopolamine treated rats (P-value=0.09). Surprisingly, in the second session, the PS-ω3 conjugate fed group presented a very different behavior. It seemed that there was no lag in the learning of the repositioned platform for PS-ω3 conjugate-fed rat treated with the anti-muscarinic drug (P-value=0.002 comparing with or without scopolamine at $t_{5-6}$). Finally, though there was no significant change between the latency time at the end of this session ($t_{7-8}$) following scopolamine treatment (P-value=0.36), there was a mild tendency to reduced levels comparing with MCT-fed rats (P-value=0.13).

In conclusion, rats fed PS-ω3 conjugate displayed reduced scopolamine-induced amnesia, and thus better spatial memory. In addition, these rats were less conservative and more adventurous in studying the maze in the absence of the platform. This behavior pattern could not be mimicked by the supplementation of PS having considerably different fatty acids composition or by providing comparable LC-PUFA supplement; however attached on the TG backbone, or even by physical mixture of these two active ingredients.

Following these memory and learning assessments, lipids levels were evaluated in different tissues. First, characterization of phospholipids distribution in lipids extract taken from rats' liver suggested that PS supplementation for three months, irrespective of its source (SB-PS or PS-ω3 conjugate) induced a distinct increase in the levels of phosphatidylcholine (PC) (FIG. 4), comparing with MCT or fish oil fed rats (P-value=0.05). These observations are consistent with early studies describing the key role played by the liver in the metabolism of phospholipids and fatty acids. Next, lipids were extracted from brain tissues of the treated rats, followed by determination of the fatty acid composition of the phospholipids fraction (Table 2). The most obvious effect of the different supplementation was the augmented levels of DHA (ANOVA P-value=0.05). The most prominent DHA accretion in the rats' brain was obtained following PS-ω3 conjugate treatment, with respect to the levels presented by MCT or SB-PS (P-value=0.01 and 0.02, respectively). Moreover these elevated DHA levels were shown to be statistically significantly higher than what was obtained by the supplements containing fish oil derived fatty acids, i.e. fish oil and fish oil+SB-PS mixture (P-value=0.03 and 0.09, respectively).

Aging is a physiological process whereby DHA levels diminish in the brain. This has been further correlated with a decline of cognitive functions as learning and memory. In a recent study [Barceló-Coblijn et al. (2003) *Proc. Natl. Acad. Sci. USA.* 100:11321-11326] 2- and 24-month-old rats were fed with fish oil (11% DHA) for one month. Although the brain DHA levels were increased by 10-15% in the old rats, which was sufficient to restore DHA to the normal levels, it did not improve the learning performance in the Morris water maze test as for the compared young rats. In previous studies of DHA transport to target cells in humans, by using $^{13}$C-labeled fatty acid esterified to triglycerides (TG) or phospholipids (PL) backbone, predominantly to the sn-2 position [Brossard et al. (1997) *J. Lipid Res.* 38:1571-1582; Lemaitre-Delaunay et al. (1999) *J. Lipid Res.* 40:1867-1874] it was demonstrated that the latter provided a putatively more available source of DHA for brain accretion.

In the present study, there was a 17% increase in the DHA level following fish oil supplementation as compared with MCT-fed rats. However, feeding PS-ω3 conjugate resulted in a 42% increase (~3-fold more) of DHA levels in the brain. Moreover, while PS-ω3 conjugate-fed rats demonstrated an evident effect in maintaining reference and working memory, despite scopolamine sedation, fish oil supplementation had only limited impact on these rats' performance in the maze. Finally, the fact that a physical mixture of fish oil, having similar content of DHA/EPA as PS-ω03 conjugate, with SB-PS, in a comparable PS concentration but with different fatty acids composition, resulted in an 15% increase in brain DHA levels (~3-fold less than PS-ω03 conjugate-fed rats), demonstrates that indeed the PS-ω3 conjugate of the invention serves as a better preparation for the delivery of these LC-PUFA to brain tissues. Furthermore, it is suggests a different metabolic fate to LC-PUFA esterified to TG or PL, even if the LC-PUFA attached to the TG backbone were consumed simultaneously with PL that do not contain any LC-PUFA.

TABLE 2

Effect of dietary LC-PUFA from different sources on the fatty acids profile of cerebral phospholipids from male Wistar rats.

| Fatty acids | MCT | LC-PUFA | SB-PS | Fish oil + PS mixture | PS-ω3 conjugate |
|---|---|---|---|---|---|
| C16:0 | 12.9 ± 1.4 | 14.6 ± 4.7 | 13.7 ± 4.7 | 10.8 ± 3.5 | 13.6 ± 4.4 |
| C16:1 | 1.0 ± 0.7 | 1.0 ± 0.3 | 1.5 ± 0.4 | 1.3 ± 0.6 | 1.5 ± 0.8 |
| C18:0 | 17.9 ± 1.0 | 20.1 ± 1.3* | 17.2 ± 2.8 | 17.7 ± 3.9 | 18.0 ± 5.5 |
| C18:1 (n – 9) | 36.5 ± 1.8 | 32.0 ± 2.8* | 37.0 ± 6.8 | 36.6 ± 7.8 | 30.7 ± 4.1* |
| C18:1 (n – 7) | 3.7 ± 0.5 | 4.3 ± 0.2* | 4.0 ± 0.3 | 4.1 ± 0.4 | 4.8 ± 1.5 |
| C18:2 | 7.2 ± 0.7 | 4.5 ± 0.6** | 7.1 ± 2.6 | 6.8 ± 3.4 | 5.1 ± 2.7 |
| C20:1 | 2.5 ± 0.5 | 2.9 ± 0.8 | 2.1 ± 0.4 | 2.8 ± 0.6 | 2.3 ± 0.3 |
| C22:6 | 12.3 ± 1.7 | 14.6 ± 0.6* | 12.4 ± 3.2 | 14.1 ± 3.8 | 17.5 ± 2.4** |
| C24:1 | 3.4 ± 1.0 | 3.3 ± 1.3 | 2.8 ± 0.9 | 3.2 ± 0.9 | 2.0 ± 1.2* |
| rest | 2.7 ± 0.1 | 2.8 ± 0.4 | 2.1 ± 0.9 | 2.5 ± 0.9 | 4.5 ± 3.0 |

Fatty acids from the purified phospholipids fraction of rats cortices were analyzed by gas-liquid chromatography. The major fatty acids are expressed as % of total fatty acids in the phospholipids.
Values represent mean ± S.D. of four different rats per treatment.
Statistical significance between different supplements and MCT group is presented as follows:
*P < 0.05;
**P < 0.01.

The difference in the DHA levels between the two omega-3 groups suggests enhanced bioavailability of DHA when esterified to the backbone of phospholipids rather than to triglycerides.

Note that DHA accretion in the cortices of both PS-ω3 conjugate and fish oil fed rats is accompanied with a statistically significant decrease in the levels of oleic acids and to somewhat lower extent of linoleic acid (Table 2) in the phospholipids fraction. Similar changes in the ratios of the fatty acids profile was demonstrated by others, by feeding rodents with dietary fats enriched with LC-PUFA [Yamamoto et al. (1988) *J. Lipid Res.*; 28: 144-151]. These alterations in fatty acids profile seemed to be as a result of fish oil-derived fatty acids supplementation as the SB-PS fed rat cortices profile was similar to the MCT.

In conclusion, the inventors demonstrates that PS-ω3 conjugate orally administered at a low dosage enables elderly rats to be less affected by anti-muscarinic drug, and more adventurous. In other words, the PS-ω3 conjugate-treated group presented increased performance of its memory functions and reduced anxiety. Further, DHA accretion levels were higher when attached to the backbone of PS, rather than as fish oil, possibly due superior bioavailability.

Example 3

PS.ω3 Conjugate in the Treatment of ADHD Children

Method
Study Design

In a randomized, double-blind, placebo-controlled parallel design 60 ADHD children (3:1 boys:girls), aged 9±1-old years, were fed for three months with fish oil (250 mg/d EPA+DHA, wherein the level of EPA is higher than the level of DHA), PS-ω3 conjugate (300 mg/d PS and 250 mg/d EPA+DHA, wherein the level of EPA is higher than the level of DHA) or control oil (canola oil), emulsified in dairy chocolate spreads (see Table 3).

No stimulant medication or other dietary supplements were administered to these subjects during feeding period. The continuous performance test, Test of Variables of Attention (T.O.V.A™) [Greenberg L M and Waldman I D (1993) *J Child Psychol Psychiatry*. 34(6):1019-1030] was tested as an objective evaluation of cognitive performance and Conners' abbreviated symptoms questionnaire as a subjective evaluation of the change in hyperactivity, inattention and oppositional behavior. In addition, 5 ml of blood were drawn from a peripheral vein at baseline and endpoint of the feeding period, to evaluate omega-3 LC-PUFA incorporation into blood compartments.

The Test of Variables of Attention (T.O.V.A.)

T.O.V.A.™ is a continuous performance test (CPT) that provides objective and valid information regarding ADHD diagnosis. In this test, the stimulus is a computer presented square containing a square hole near the top or bottom edge. The square with the hole in the top is the target. The participant is instructed to respond by pressing a hand-held microswitch when the hole is on the top and not to respond when the hole is on the bottom. The stimuli are presented for 200 milliseconds at the rate of 30 per min. The duration of the test is 22.5 min. Targets are present on 22.5% of trials during the first half of the test and 77.5% of the trials during the last half. The variables measured were: omission errors or failure to respond to the designate target, which is interpreted as a measure of inattention; commission errors or incorrect response to the non-target, which is considered as a measure of impulsivity; response time (in milliseconds) or the latency time required to respond correctly to the target stimulus, which is interpreted as a measure of information processing; response time variability (the standard deviation of response times), which is interpreted as an index of consistency of attention; the number of multiple responses to target or reflection of neurological status, which is interpreted as a measure of motor hyper-responsivity; and the number of anticipatory responses (very short latency responses), which represents guessing and could be interpret as a measure of impulsivity as well as validity of the results. These results were further compared with normal, same-gender, same-age and average IQ group, to be reported as standard deviation. Multiple responses and anticipatory responses were left as raw scores because no normative data were available. The standard deviation indicates the extent of a problem, i.e. a more negative value point at specific parameter severity and conversely the more positive deviation from norm value suggest better than average performance. Total TOVA score includes the response time, d prime or response sensitivity, which is used to interpret the rate of deterioration of performance over time and response time variability. This score, also considered as an ADHD index score, serves as an indication of the degree of similarity in performance between the assessed children and normative samples. According to the TOVA professional manual guide [Greenberg L M and Kindschi C L. (1996) *T.O.V.A. Test of Variables of Attention: clinical guide*. Los Alamitos: Universal Attention Disorders Inc.], total score lower than −1.8 SD indicates high probability of ADHD symptoms. This parameter was used for screening, as the enrolment criteria.

Behavioral Ratings by Parents

Prior to the initial interview, at a mead-term time point and upon feeding phase termination, mothers or mother substitutes were asked to complete the Conners' abbreviated symptoms questionnaire. On the Conners' test the ratings on Factor I (Conduct Problems), Factor II (Hyperactivity), Factor III (Inattentive-Passive), and the Hyperkinesis Index were normalized to the age and sex of the subject, and formed into an overall score [Goyette, C. H. et al. (1978) *J. Abnorm. Child Psychol*. 6(2), 221-236].

Lipid Analysis

Non-fasting blood samples (5 ml) were drawn from a peripheral vein at the beginning and the end of the feeding period. The samples were separated for plasma and red blood cells, washed and stored in −80° C. for lipid analysis. The lipid fraction of both the plasma and the red blood cells were extracted using a modified version of the techniques previously described. Briefly, 5 ml of diluted plasma sample were first homogenized using a polytron homogenizer in methanol, followed by chloroform extraction (2:1, v:v) at room temperature and protein determination using Bradford reagent. The samples were filtered and washed with 0.25% KCl solution. The chloroform lower phase was then evaporated under vacuum, and the lipids weighted. The phospholipids were purified by 1D-TLC on silica gel plates (Merck 60) using diisopropylether as the developing solvent. The TLC plate was subsequently air dried, and phospholipids at the spotting area were scraped into vials. Total phospholipids aliquots were further converted to methyl esters by transmethylation 1 hr at 90° C. with methanolic/HCl, and the fatty acids composition of the different samples was determined by gas-liquid chromatography.

Results

There were no statistically significant differences between the three groups, in general characteristics as well as in the objective (TOVA) and subjective (parental behavioral assessments) analyses at baseline (Table 3). Likewise, there are no differences in the baseline values of the fatty acid pattern of the plasma phospholipids (Table 4). The gender distribution of ADHD is conservatively considered to be 2:1 to 4:1 male-to-female ratio. In this study the ratio average was 3:1, thus the sample should be consider representative. As dictated by the study protocol, all the subjects had demonstrated an ADHD index score lower than −1.8. Moreover, the z score means in baseline of all tested subjects clearly demonstrate that in all but errors of commission there are marked deviations from the scores of age- and gender-matched asymptomatic children. This notion is being further corroborated by the results of the behavioral assessments (Table 3). In addition, having all subjects presenting comparable fatty acids profile at baseline suggests that there is no subpopulation of low LC-PUFA status ADHD children [Burgess, J. R. et al. (2000) *Am. J. Clin. Nutr*. 71(1 Suppl):327S-330S] among the subjects groups.

TABLE 3

Characteristics of the three treatment groups at the baseline of completers

| Characteristic | Canola oil | Fish oil | PS-$\overline{\omega}$3 conjugate | P |
|---|---|---|---|---|
| n | 21 | 21 | 18 | |
| Age (yr)[a] | 9.31 ± 1.28 | 9.40 ± 1.06 | 9.17 ± 1.27 | NS |
| Gender (% males/female) | 71.4/28.6 | 71.4/28.6 | 83.3/16.7 | NS |
| Behavioral assessments (parents) | | | | |
| Conners' abbreviated symptoms questionnaire | 15.05 ± 6.2 | 17.10 ± 5.26 | 14.33 ± 6.67 | NS |
| Achenbach' Child Behavior Checklist for Ages 4-18 | 9.95 ± 4.47 | 8.95 ± 3.84 | 10.00 ± 5.10 | NS |
| Attention performance and cognitive abilities (TOVA[b]) | | | | |
| ADHD index | −4.93 ± 2.96 | −5.69 ± 3.64 | −4.53 ± 2.41 | NS |
| Errors of omission | −1.63 ± 1.71 | −1.62 ± 1.69 | −1.31 ± 1.76 | NS |
| Errors of commission | 0.12 ± 1.33 | −0.02 ± 1.34 | 0.13 ± 0.81 | NS |
| Total response time | −2.00 ± 1.06 | −2.10 ± 1.20 | −1.72 ± 1.22 | NS |
| Response time variability | −1.88 ± 1.18 | −2.22 ± 1.08 | −1.81 ± 1.07 | NS |
| Multiple responses[c] | 9.00 ± 13.29 | 10.67 ± 14.24 | 6.00 ± 7.81 | NS |
| Anticipatory responses[c] | 1.57 ± 1.63 | 1.75 ± 1.85 | 1.52 ± 1.57 | NS |

[a]Mean ± SD. Baseline characteristics analysis are performed using analysis of variance (ANOVA) model for continuous variables and Kruskal-Wallis test for non-parametric variables, except for gender in which Fisher exact test was used
[b]Test of variable of attention; z scores at baseline
[c]Non-normalized scores

TABLE 4

Fatty acids composition of plasma phospholipids (as % of total fatty acids)

| FA | Canola oil | | Fish oil | | PS-$\overline{\omega}$3 conjugate | |
|---|---|---|---|---|---|---|
| | Baseline | Endpoint | Baseline | Endpoint | Baseline | Endpoint |
| Total saturated | 39.41 ± 2.51 | 38.83 ± 2.99 | 39.03 ± 3.53 | 40.57 ± 3.86 | 38.53 ± 3.67 | 39.49 ± 3.36 |
| Total monosaturated | 11.08 ± 1.85 | 10.81 ± 1.40 | 10.99 ± 1.11 | 10.18 ± 1.11 | 12.42 ± 2.75 | 10.66 ± 1.10 |
| 18:1ω9 | 8.19 ± 1.57 | 7.78 ± 1.19 | 8.03 ± 1.00 | 7.20 ± 1.15[c] | 8.98 ± 1.59 | 7.70 ± 1.03[c] |
| Total ω6 | 34.72 ± 4.08 | 35.68 ± 3.18 | 34.94 ± 4.11 | 32.59 ± 4.39[b] | 34.3 ± 1.4 | 34.7 ± 1.1 |
| 18:2ω6 | 19.44 ± 3.22 | 20.24 ± 3.15 | 19.86 ± 2.42 | 19.71 ± 3.30 | 18.38 ± 4.08 | 21.10 ± 2.59[b] |
| 20:4ω6 | 10.43 ± 1.35 | 11.13 ± 1.26[a] | 10.09 ± 2.35 | 8.98 ± 2.16[a] | 11.23 ± 2.63 | 9.51 ± 2.25[b] |
| 22:4ω6 | 0.61 ± 0.12 | 0.61 ± 0.18 | 0.74 ± 0.28 | 0.47 ± 0.12[d] | 0.79 ± 0.19 | 0.54 ± 0.15[d] |
| Total ω3 | 6.40 ± 1.99 | 6.22 ± 1.61 | 5.47 ± 1.53 | 7.01 ± 1.99[b] | 5.87 ± 1.49 | 7.98 ± 2.19[c] |
| 20:5ω3 | 0.70 ± 0.51 | 0.64 ± 0.58 | 0.60 ± 0.59 | 0.89 ± 0.39[a] | 0.42 ± 0.18 | 0.92 ± 0.43[d] |
| 22:5ω3 | 0.99 ± 0.34 | 0.88 ± 0.26 | 0.91 ± 0.30 | 1.06 ± 0.28 | 1.01 ± 0.34 | 1.18 ± 0.26[a] |
| 22:6ω3 | 4.71 ± 1.67 | 4.70 ± 1.34 | 3.96 ± 1.37 | 5.06 ± 1.77[b] | 4.45 ± 1.52 | 5.88 ± 1.95[b] |
| Ratios | | | | | | |
| ω6/ω3 | 5.92 ± 1.90 | 6.26 ± 2.33 | 6.92 ± 2.28 | 4.94 ± 1.26[d] | 6.19 ± 1.67 | 4.59 ± 1.02[c] |
| 20:5ω3/20:4ω6 | 0.062 ± 0.036 | 0.054 ± 0.053 | 0.070 ± 0.080 | 0.106 ± 0.066[c] | 0.044 ± 0.040 | 0.107 ± 0.047[d] |

Mean ± SD.
Changes in the variables were tested by Students t-test to determine statistical differences within the tested groups.
[a]$P < 0.1$;
[b]$P < 0.05$;
[c]$P < 0.01$;
[d]$P < 0.001$ Three months of PS-$\overline{\omega}$3 conjugate supplementation resulted in a pronounced increase in the EPA, docosapentaenoic acid, (DPA; 22:5 ω3) and DHA contents (159±41%; 26±10%; 34±7%, respectively; see Table 4). This marked increase of plasma phospholipids omega-3 fatty acids content by the PS-$\overline{\omega}$3 conjugate administration was accompanied by a significant 15% and 30% decline in the content of the ARA and adrenic acid, respectively. This combined effect on the omega-3 and omega-6 fatty acids levels as a result of the supplementation by PS-$\overline{\omega}$3 conjugate induced a significant and distinct reduction of ω6/ω3 ratio (37±8%). The change in the ratio between EPA to ARA, was suggested to be directly correlated with the severity of depressive symptoms in patients with moderate to severe depression as well as aggression in children [Itomura, M. et al. (2005) *J Nutr Biochem.* 16(3):163-171; Young, G. S. et al. (2005) *Reprod Nutr Dev.* 45(5):549-558]. Both conditions show a high ratio of co-morbidity with ADHD, and both were shown to be affected by fish oil supplementations. In the present study, feeding with PS-$\overline{\omega}$3 conjugate induced a striking reduction effect of this ratio by 223±55%.

Comparing the scores obtained by Conners' abbreviated symptoms questionnaire, a significant effect of treatment groups was found between the baseline or from midterm to endpoint (P-value=0.004 and 0.001, respectively, by ANOVA with repeated measurements). Though a distinct placebo effect (~−2 pts.) was observed, administration of PS-ω̄3 conjugate to ADHD children induced a notable trend in reducing Conners' abbreviated symptoms questionnaire (−5.00±8.32; 95% CI −9.14, −0.86). This remarkable effect (~30%) exceed what was previously published for administration of olive oil (16.4%) or LC-PUFA (23.2%) [Stevens et al. (2003) *Lipids.;* 38:1007-21].

The most prominent result obtained in this study was the extent of change induced by PS-ω̄3 conjugate consumption from baseline levels in the CPT, as characterized by the ADHD index score (see Table 5). The statistical analyses show that supplementation with PS-ω̄3 conjugate resulted in a pronounced treatment effect (reduction of 94±15%) compared to control canola oil (increase of 14±17%). Improvement of the ADHD index that exceed 80% or 2.5 SD as previously reported for methylphenidate [Alhambra, M. A. et al. (1995) *J Neurotherapy.* 1(2):39-43] or modafinil [Rugino T. A. and Copley T. C. (2001) *J. Am. Acad. Child Adolesc. Psychiatry* 40(2):230-235], respectively, could be considered as a stimulant-induced effect. In the present study, consumption of PS-ω̄03 conjugate resulted in marked reduction of 3.35 SD, from −4.53 SD to −1.18 SD, in this index. Moreover, a change in performance of about 1 SD in the subcategories of the TOVA following stimulants medications was suggested to be clinically significant [Greenberg L M and Kindschi C L. (1996) *T.O.V.A. Test of Variables of Attention: clinical guid.* Los Alamitos: Universal Attention Disorders Inc.]. Indeed, in all the normalized parameters, i.e. errors of omission, errors of commission, total response time and response time variability, known to be positively affected by stimulants administrations, there is a significant effect of PS-ω̄3 conjugate of 0.72-1.01 SD (see Table 5). In addition, treatment effect was also established for total response time and response time variability. It is interesting to indicate that in a recent publication, these parameters demonstrated greater temporal stability and individual test-retest score agreement as compared to errors of omission and commission [Voigt R. G. et al. (2001) *J Pediatr.* 139(2):189-196]. Time and variability were also reported to accurately differentiate between ADHD and control children [Howard B V et al. (2006) *Jama.* 295(6):655-666]. Finally, there was a significant diet effect on the multiple responses parameter, which was previously suggested to be statistically different in ADHD from the others and even weakly correlated to the attention parameter in the ADHD comprehensive teacher's rating scale [Forbes G B. (1998) *J Clin Psychol.* 54(4):461-476]. Similar tendency was observed for the anticipatory responses parameter. In both cases there was a significant and positive effect of fish oil and PS-ω̄3 conjugate (see Table 5).

TABLE 5

Changes in T.O.V.A. scores from baseline for different treatments

| TOVA scores | Absolute change[a] | P for differences within group[b] | P for differences between group[c] |
|---|---|---|---|
| ADHD index score | | | |
| Canola oil | −0.45 ± 2.51[X] | NS | 0.0001 |
| Fish oil | 1.72 ± 1.67[Y] | 0.0001 | |
| PS.-ω3 conjugate | 3.35 ± 1.86[Z] | 0.00004 | |

TABLE 5-continued

Changes in T.O.V.A. scores from baseline for different treatments

| TOVA scores | Absolute change[a] | P for differences within group[b] | P for differences between group[c] |
|---|---|---|---|
| Errors of omission | | | |
| Canola oil | 0.33 ± 1.44 | NS | NS |
| Fish oil | 0.37 ± 1.07 | 0.03 | |
| PS-ω3 conjugate | 0.90 ± 1.43 | 0.05 | |
| Errors of commission | | | |
| Canola oil | −0.06 ± 1.32 | NS | 0.1 |
| Fish oil | 0.53 ± 1.18 | NS | |
| PS-ω3 conjugate | 0.75 ± 1.09 | 0.006 | |
| Total response time | | | |
| Canola oil | −0.02 ± 1.17[X] | NS | 0.05 |
| Fish oil | 0.24 ± 0.71[XY] | 0.05 | |
| PS-ω3 conjugate | 0.72 ± 0.69[Y] | 0.04 | |
| Response time variability | | | |
| Canola oil | −0.30 ± 1.44[X] | NS | 0.004 |
| Fish oil | 0.63 ± 0.86[Y] | 0.01 | |
| PS-ω3 conjugate | 1.01 ± 1.25[Y] | 0.02 | |
| Multiple responses | | | |
| Canola oil | 5.33 ± 14.04[X] | NS | 0.035 |
| Fish oil | −5.05 ± 14.75[Y] | 0.05 | |
| PS.-ω3 conjugate | −2.56 ± 9.41[XY] | 0.05 | |
| Anticipatory responses | | | |
| Canola oil | 0.76 ± 2.29 | NS | 0.058 |
| Fish oil | −0.49 ± 1.84 | 0.05 | |
| PS.-ω3 conjugate | −0.59 ± 1.70 | 0.05 | |

60 ADHD children were fed for 91 ± 10 days with canola oil, fish oil or PS.-ω3 conjugate, emulsified in chocolate spreads. Continuous performance test (T.O.V.A.) was performed prior to- and following the feeding phase, as described in methods.
[a]Mean ± SD of endpoint minus baseline SD values, but multiple responses and anticipatory responses, which are non-standard scores A positive change indicates improvement, except for multiple responses and anticipatory responses, which are non-standard scores
[b]Students t-test was used to determine statistical differences between means of tested groups
[c]The effect of different supplements was tested by Kruskal-Wallis followed by post hoc testing for differences between means using Gabriel and Games-Howell tests, which adjust $\alpha = 0.05$ for multiple comparison (group* time interaction).
[X-Z]Means with similar superscripts are not statistically different.

The effect size for the ADHD children which received PS-ω̄3 conjugate for 88±3 days of the primary assessment, i.e. the improvement in the ADHD index score in TOVA, was ~60% (see FIG. 5). This is the rate of ADHD children that completed the study and were characterized by TOVA as asymptomatic ($\geq$−1.8 SD). This effect, which is considered moderate to large in magnitude, was statistically significant different from that presented by control canola oil, while the fish oil treatment could not be distinguished from the control. As a CPT tool the TOVA was suggested to serve as useful objective measure of treatment efficacy, rather than a diagnostic tool [Howard et al. (2006) id ibid.; Forbes (1998) id ibid.]; thus these observations could be associated to the dietary matrix beneficial clinical outcomes. This effect strongly presents PS-ω̄03 conjugate as an agent for the treatment of cognitive conditions, in particular with respect to inattention and impul sivity. Interestingly, the levels of DHA and EPA incorporation into the triglycerides and cholesterol ester fractions of the plasma were evaluated in a sample of the tested ADHD children (n=20). It appeared that there was relatively very low levels of these fatty acids in all groups triglycerides fraction (P<NS), suggesting that the last supplements were consumed more than 12 h prior to the phlebotomy. This further indicates that the effect of the PS-ω3 conjugate of the invention on ADHD children persists beyond the period of the supplement administration. DL-threo-Methylphenidate, on the other hand, was shown to be readily absorbed after oral administration, with maximum plasma concentrations from 1 to 3 h, varying significantly between individuals; however its $t_{1/2}$ is at approximately 2.6 to 3 h, due to rapid metabolism. Alternatively, PS-ω3 conjugate supplementation could provide a comparable effect for most of the daytime hours without the requirement to use slow-release techniques to overcome high deterioration rate.

This study was designed, in part, to evaluate the relationship between proportions of LC-PUFA incorporation to the blood compartment and the severity of behavioral symptoms. The changes in the proportion of the key Omega 3 and Omega 6 fatty acids in the plasma phospholipids was compared with the changes in the scores of the ADHD index as well as the TOVA scores subcategories. For the normalized TOVA scores (see Table 3) a negative correlation between fatty acid and a behavioral score indicates that a positive change in the biochemical parameter is associated with a positive change in the behavioral parameter, whereas a negative correlation indicates the reverse. For the non-normalized TOVA scores, it is the other way around, as for these outcomes measure, decreasing values signifies better performance. In FIG. 6, the changes in EPA/ARA ratio were negatively correlated with the change in ADHD index for both the canola oil and PS -ω3 conjugate. However these two groups seemed to present a distinct pattern of scattered data points: while only 33% of the ADHD children fed with the control oil improved their ADHD index, irrespectively of the impact on the final score, and 23% increased their EPA/ARA ratio, 94% of the ADHD children fed with the PS-ω3 conjugate of the invention demonstrated an improved ADHD score and EPA/ARA ratio increase. Results in the fish oil-fed children showed a non-significant correlation. Moreover, it appeared that PS-ω3 conjugate consumption outcomes on fatty acid ω3 and/or ω6 pattern change in plasma phospholipids could be further correlated with most of the TOVA subcategories (Table 6). The positive effect of PS-ω3 conjugate on inattention and impulsivity symptoms in ADHD could be correlated to the ω3 increase and the ω6 decrease in the plasma phospholipids fatty acids pattern, such correlation was not found for the control canola oil or the fish oil supplementation.

Taking together with what was demonstrated in Example 2, providing PS-ω3 conjugate results in a better bioavailability of LC-PUFA, and especially omega-3, to brain tissues. In both cases though comparable levels of DHA and EPA were provided on TG or PS backbone, the positive correlation between the behavioral alteration and the LC-PUFA tissues accretion was exclusively identified in the PS-ω3 conjugate-treated group. Interestingly, previous attempts of EPA+DHA supplementation to ADHD patients failed to demonstrate comparable beneficial effect in an objective test, supporting the idea that the PS-ω3 preparation utilized in the present study is superior in delivering LC-PUFA to the subjects consuming it.

Example 4

Effect of PC-DHA Consumption in ApoE° Mice

Methods
Animal Diet

Apolipoprotein E deficient (ApoE°) mice [Hayek T. et al. (1994) *Biochem. Biophys. Res. Commun.* 201:1567-1574] at 8 weeks of age, were assigned randomly (5 mice each) to LC-PUFA enriched lecithin (30% omega-3 of total fatty acids composition; PC-DHA group) or placebo. The mice were fed, besides the regular chow diet, once every three days with either 25 μl PC-DHA or PBS, via oral gavage, during 10 weeks. Each mouse consumed approximately 5 mL of water/day, and 5 g of chow/day.
Serum Lipids Peroxidation Serum was diluted 1:4 in PBS. Serum susceptibility to oxidation was determined by incubating serum sample with 100 mM of the free radical generating compound, 2'-2'-azobis 2'-amidinopropane hydrochloride (AAPH), which is an aqueous soluble azo compound that thermally decomposes to produce peroxyl radicals at a constant rate. The formation of thiobarbituric reactive substances (TBARS) and of lipid peroxides was measured and compared to serum that was incubated under similar conditions, but without AAPH.
Results and Discussion:

ApoE° mice are widely used as an animal model for atherosclerosis as they develop severe hypercholesterolemia and atherosclerotic lesions on a chow diet. Moreover, accelerated atherosclerosis is associated with increased lipid peroxidation of plasma lipoproteins and arterial cells in these mice [Hayek T. et al. (1994) id ibid.; Keidar S. (1998) *Life Sci.* 63:1-11].

FIG. 7 shows how prolonged PC-DHA consumption by ApoE° mice resulted in a clear tendency (P<0.10) to reduce the serum susceptibility to AAPH-induced oxidation by 16% (in comparison to placebo).

Example 5

Organoleptic Issues

The utilization of omega-3 lipids in a variety of applications, and especially as an ingredient of functional foods, is hindered due to their distinct fish odor. Thus, another advantage of the omega-3 enriched phospholipids preparations of the invention is that they have reduced odor or taste of omega-3 acyl moieties, due to the covalent binding of these groups to the PS backbone. This increases the vapor pressure of these materials, hence reducing their distinct aroma. Thus, the covalent binding of the omega-3 fatty acids to the phospholipid backbone, especially PS, alters and improves their taste properties. Moreover, the PS preparation of the invention also offers enhanced stability to the oxidation sensitive omega-3 fatty acids. Phospholipids in general, and PS in particular, are known to act as anti-oxidants and stabilizers [Lyberg A M. et al. (2005) *Lipids.* 40:969-979].

These benefits make this novel phospholipids' preparation of the invention highly beneficial and important in a variety of applications and especially in functional foods, where stability, aroma and taste are fundamental requirements.

Furthermore, these novel preparations can be formulated with additional lipids for an even enhanced bio-functionality and efficacy.

The starting compound used for the above-mentioned clinical trial in ADHD patients, was LC-PUFA enriched PS mixed with fish oil. Originally, this product and the control fish oil were formulated in food products like energy bars; however the responses from expert panels were less encouraging, pointing at severe organoleptic problems. In order to overcome this taste barrier the PS -ω3 conjugate product of the invention was de-oiled.

The end-product of this process was a paste that when reformulated with either inert or dominant-organoleptic saturated fats could be easily formulated in chocolate bars, chocolate spread, chocolate coated cornflakes, low-fat dairy products or concentrated milk. Each one of these formulations had an evidently reduced organoleptic objection from both the expert panels and the trial volunteers.

The polar lipids derivatives of PUFA, such as the PS-PUFA derivatives have exhibited high stability as a preparation and additionally in several food applications, used in the clinical trials of this invention. This stability, of these sensitive compounds is emerging from the covalent combination of phospholipids, known in the past to be used as preservatives and of the un-stable PUFA moieties.

The above-mentioned PS-$\overline{\omega}$3 conjugate containing products utilized for the clinical studies were tested for their shelf-life and stability in room temperature. The enriched PS-$\overline{\omega}$3 conjugate formulated in condensed milk (1 g product per 10 ml milk) was analyzed by $^{31}$P-NMR for stability in cycles of freeze-thawing for a week, and was found to be stable. In the second phase, PS-$\overline{\omega}$3 conjugate in a chocolate paste matrix (0.75 g product per 20 g chocolate spread) was tested for stability after two weeks storage in room temperature. This formulation also presented a stable percentage of PS, in $^{31}$P-NMR analysis. In conclusion, the inventors were able to establish that $\overline{\omega}$-3 containing phospholipids are highly stable in room temperature, as well as in freezing-thawing cycles, as oppose to $\overline{\omega}$-3 containing triglycerides known to rapidly decay after antioxidant consumption.

TABLE 6

Correlations between changes in TOVA sub-categories scores and changes in plasma phospholipids fatty acids levels

| | 22:6ω3 | | | 20:5ω3/20:4ω6 | | | ω3 | | | ω3/ω6 | | |
|---|---|---|---|---|---|---|---|---|---|---|---|---|
| | Canola oil | Fish oil | PS-$\overline{\omega}$3 | Canola oil | Fish oil | PS-$\overline{\omega}$3 | Canola oil | Fish oil | PS-$\overline{\omega}$3 | Canola oil | Fish oil | PS-$\overline{\omega}$3 |
| Errors of omission | .232 | .385 | −.599[a] | −.285 | .127 | −.622[a] | .032 | .384 | −.738[b] | .007 | .366 | −.716[b] |
| Errors of commission | .335 | −.077 | −.543[a] | −.265 | −.083 | −.238 | .275 | −.059 | −.548[a] | .165 | −.104 | −.520[a] |
| Total response time | .477[a] | .141 | −.200 | −.498[a] | .201 | −.522[a] | .260 | .187 | −.248 | .215 | .186 | −.388 |
| Response time variability | .243 | −.225 | −.467 | −.556[a] | −.278 | −.403 | .007 | −.272 | −.467 | −.040 | −.317 | −.457 |
| Multiple responses | −.252 | .592[a] | .494[a] | .304 | .221 | .335 | −.170 | .561[a] | .507[a] | −.084 | .596[a] | .748[b] |
| Anticipatory responses | −.436 | .393 | .603[a] | .402 | .553[a] | .500[a] | −.308 | .517[a] | .708[b] | −.172 | .560[a] | .670[b] |

[a,b]Pearson correlation coefficients: [a]P < 0.05, [b]P < 0.01

The invention claimed is:

1. A preparation comprising serine glycerophospholipids which comprise a mixture of serine glycerophospholipids comprising eicosapentaenoic acid (EPA) and serine glycerophospholipids comprising docosahexaenoic acid (DHA), wherein each such serine glycerophospholipid comprising EPA and each such serine glycerophospholipid comprising DHA has the formula (I):

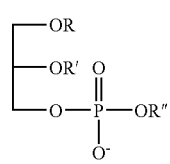

wherein R″ is serine;
wherein one of R or R′ is acyl EPA or acyl DHA and the other of R or R′ is hydrogen or an acyl group;
wherein the percent by weight of EPA is higher than the percent by weight of DHA in such mixture of serine glycerophospholipids;
wherein the combined amount of EPA and DHA present in such mixture of serine glycerophospholipids constitutes 10-50% by weight of the total fatty acid content of the serine glycerophospholipids in said preparation; and
wherein the mixture is not identical to naturally occurring human or mammalian brain phosphatidylserine (PS).

2. The preparation of claim 1, wherein said glycerophospholipid conjugate is prepared by enzymatic transphosphatidylation of a lipid source, said source being selected from the group consisting of a marine, a plant, an animal and a microorganism source.

3. A pharmaceutical composition comprising the preparation of claim 1 and at least one pharmaceutically acceptable additive, diluent or excipient.

4. The pharmaceutical composition of claim 3, further comprising at least one additional pharmaceutically active agent.

5. The pharmaceutical composition of claim 3, wherein said composition is in the form of a tablet, capsule, injectable or patch.

6. A nutraceutical composition comprising the preparation of claim 1.

7. The nutraceutical composition of claim 6, in the form of softgel capsule, tablet, syrup, or other dietary supplement delivery system.

8. A functional food article comprising the preparation of claim 1.

9. The food article of claim 8, wherein said article is a dairy product, ice cream, biscuit, soy product, cake, pastry, bread, sauce, soup, prepared food, instant food, frozen food, condiment, confectionery, oil, fat, margarine, spread, filling, cereal, instant product, drink, shake, infant formula, infant food, mashed fruit, vegetable, cereal, bar, snack, candy or chocolate product.

* * * * *